(12) United States Patent
Sutcliffe et al.

(10) Patent No.: US 6,814,967 B2
(45) Date of Patent: Nov. 9, 2004

(54) ANTIBODIES TO CORTISTATIN: NEUROPEPTIDES, COMPOSITIONS AND METHODS

(75) Inventors: J. Gregor Sutcliffe, Cardiff, CA (US); Luis De Lecea, Del Mar, CA (US); Steven J. Henriksen, Solana Beach, CA (US); George R. Siggins, Del Mar, CA (US)

(73) Assignee: The Scripps Research Institute, La Jolla, CA (US)

( * ) Notice: Subject to any disclaimer, the term of this patent is extended or adjusted under 35 U.S.C. 154(b) by 289 days.

(21) Appl. No.: 09/766,396

(22) Filed: Jan. 18, 2001

(65) Prior Publication Data

US 2002/0013456 A1 Jan. 31, 2002

Related U.S. Application Data

(60) Division of application No. 08/857,389, filed on May 15, 1997, now Pat. No. 6,479,642, which is a continuation-in-part of application No. 08/648,322, filed on May 15, 1996, now Pat. No. 6,074,872.

(51) Int. Cl.[7] .......................... A61K 39/395; C12N 5/16
(52) U.S. Cl. ............................... 424/139.1; 424/133.1; 424/145.1; 424/158.1; 435/336; 530/387.9; 530/388.24; 530/389.2
(58) Field of Search .......................... 424/130.1, 133.1, 424/141.1, 145.1, 158.1, 139.1; 435/326, 336; 530/387.1, 388.1, 387.9, 388.24, 389.2

(56) References Cited

U.S. PATENT DOCUMENTS 5,426,099 A    6/1995    Komisaruk et al. ........... 514/13

FOREIGN PATENT DOCUMENTS

EP        0 197 558        10/1986

OTHER PUBLICATIONS

Geysen et al. J. Molecular Recognition 1: 32–41, 1988.*
De Lecea L. et al.: "A cortical neuropeptide with neuronal depressant and sleep–modulating properties" NATURE, 381:242–245 (May 16, 1996).
Fukusumi S. et al.: "Identification and characterization of a novel human Cortistatin–like peptide" Biochemical and Biophysical Research Communications, 232(1):157–163 (Mar. 6, 1997).
Tostivint H. et al.: "Un deuxième gène codant pour la somatostatine est exprimè dans le cerveau" M/S (Medecine/Sciences) Mini–Synthèse, 12(10):1131–1133 (10/96).
Prospero–Garcia O et al.: "Cortistatin modulates cortical and hippocampal electrophysiological activity and sleep" Society for Neuroscience Abstracts: 26th Annual Meeting, Washington, D.C., USA., 22(1–3):1152 (Nov. 16, 1996—Nov. 21, 1996).
De Lecea L. et al.: "Cloning mRNA expression, and chromosomal mapping of mouse and human Preprocortistatin" GENOMICS, 42(3):499–506 (Jun. 15, 1997).

* cited by examiner

*Primary Examiner*—Brenda Brumback
*Assistant Examiner*—Robert C. Hayes
(74) *Attorney, Agent, or Firm*—Townsend & Townsend & Crew LLP

(57) ABSTRACT

The present invention relates generally to nucleic acids encoding a novel neuropeptide designated cortistatin. The cortistatin nucleic acids, proteins and polypeptides thereof along with anti-cortistatin antibodies are useful in both screening methods, diagnostic methods and therapeutic methods related to modulation of sleep and disorders thereof.

8 Claims, 8 Drawing Sheets

```
                 10              30                50
        AAAGCACAGACTTCAGGTCTCCAAGGAGGATGGGTGGCTGCAGCACAAGAGGCAAGCGGC
                                        M  G  G  C  S  T  R  G  K  R  P 70              90               110
        CGTCAGCCCTCAGT CTGCTGCTGCTGCT GCTGCTCT CGGGGATCGCAGCCTCTGCCCTCC
         S  A  L  S  L  L  L  L  L  L  L  S  G  I  A  A  S  A  L  P
                                                       ↑
                 130             150              170
        CCCTGGAGAGCGGTCCCACCGGCCAGGACAGTGTGCAGGATGCCACAGGCGGGAGGAGGA
         L  E  S  G  P  T  G  Q  D  S  V  Q  D  A  T  G  G  R  R  T 190             210              230
        CCGGCCTTCTGACTTTCCTTGCCTGGTGGCATGAGTGGGCTTCCCAAGACAGCTCCAGCA
         G  L  L  T  F  L  A  W  W  H  E  W  A  S  Q  D  S  S  S  T 250             270              290
        CCGCTTTCGAAGGGGGTACCCCGGAGCTGTCTAAGCGGCAGGAAAGACCACCCCTCCAGC
         A  F  E  G  G  T  P  E  L  S  K  R  Q  E  R  P  P  L  Q  Q 310             330              350
        AGCCCCCACACCGGGATAAAAAGCCCTGCAAGAACTTCTTCTGGAAAACCTTCTCCTCGT
         P  P  H  R  D  K  K  P  C  K  N  F  F  W  K  T  F  S  S  C 370             390              410
        GCAAGTAGCCCGAGCCTGACCGGAGCCTGACCGGCCACCCTGTGAATGCAGCCGTGGCCT
         K

430
        GAATAAAGAGTGTCAAGT
```

FIGURE 1

```
CST    10  RPSALSLLLLLLLSGIAASALPLESGPTGQDSVQDATGGRRTGLLTFLAW  59
            ...  .|  ::|  |:|:.:.:  .    .  |.|:..|||  .  :  .  :  .:
SST    7   QCALAALCIVLALGGVTGAPSDPRLRQFLQKSLAAATGKQELAKYFLAEL  56
                                                    ↓                      ↓
CST    60  WHEWASQDSSSTAFEGGTPELSKRQERPPLQQ........PPHRDKKPCK  101
           :|  .  :....  .|:  ...  ..  :|  .||.         :|:      |  .||
SST    57  LSEPNQTENDALEPEDLPQAAEQDEMRLELQRSANSNPAMAPRERKAGCK  106
                                     ↑                            ↑

CST    102 NFFWKTFSSCK
           |||||||.||.
SST    107 NFFWKTFTSC
```

FIGURE 2

```
GCACCAGGCT CAGCACGTCC GAGG ATG ATG GGT GGC CGA GGC ACA GGA GGC        51
                          Met Met Gly Gly Arg Gly Thr Gly Gly
                           1                 5

AAG TGG CCC TCA GCC TTC GGG CTG CTG CTG CTC TGG GGG GTC GCA GCC       99
Lys Trp Pro Ser Ala Phe Gly Leu Leu Leu Leu Trp Gly Val Ala Ala
 10              15                  20                  25

TCC GCC CTT CCC CTG GAG AGT GGC CCT ACT GGC CAG GAC AGT GTG CAG      147
Ser Ala Leu Pro Leu Glu Ser Gly Pro Thr Gly Gln Asp Ser Val Gln
             30                  35                  40

GAA GCC ACC GAG GGG AGG AGC GGC CTT CTG ACT TTC CTT GCC TGG TGG      195
Glu Ala Thr Glu Gly Arg Ser Gly Leu Leu Thr Phe Leu Ala Trp Trp
             45                  50                  55

CAC GAG TGG GCT TCC CAA GCC AGC TCC AGC ACC CCC GTC GGA GGG GGT      243
His Glu Trp Ala Ser Gln Ala Ser Ser Ser Thr Pro Val Gly Gly Gly
             60                  65                  70

ACC CCC GGG CTG TCC AAG AGC CAG GAA AGG CCA CCC CCC CAA CAG CCC      291
Thr Pro Gly Leu Ser Lys Ser Gln Glu Arg Pro Pro Pro Gln Gln Pro
         75              80                  85

CCA CAC CTG GAT AAA AAG CCC TGC AAG AAC TTC TTC TGG AAA ACC TTC      339
Pro His Leu Asp Lys Lys Pro Cys Lys Asn Phe Phe Trp Lys Thr Phe
         90              95                 100                 105

TCC TCG TGC AAG TAA CCC CAC CCT GGG CAT AGG ACC CTG GCC ACC CTG      387
Ser Ser Cys Lys  *
                110                 115                 120

TGA GAT GCC AAC GAG ACC TGA ATA AAG ACT GTC AAT CAA C                427
              125                 130
```

FIGURE 3

```
MOUSE CST   ..........  ...GCACGAG  GCTCAGCACG  TCCGAGGATG  ATGGGTGGCC
RAT CT      ..........  .AAAGCACAG  ACTTCAGGTC  TCCAAGGAGG  ATGGGTGGCT
HUMAN CST   GGCACGAGGC  CAAACATTGA  TTTCAGGGCT  GCCAGGAAGG  AAGAGCAGCA

MOUSE CST   GAGGCACAGG  AGGCAAGTGG  CCCTCAG...  ..........  .....CCTTC
RAT CST     GCAGCACAAG  AGGCAAGCGG  CCGTCAG...  ..........  .....CCCTC
HUMAN CST   GCAGGGTGGG  AGAGAAGCTC  CAGTCAGCCC  ACAAGATGCC  ATTGTCCCCC

MOUSE CST   GG........  .GCTGCTGCT  GCTCTGGGGG  GTCGCAGCCT  CCGCCCTTCC
RAT CST     AGTCTGCTGC  TGCTGCTGCT  GCTCTCGGGG  ATCGCAGCCT  CTGCCCTCCC
HUMAN CST   GGCCTCCTGC  TGCTGCTGCT  CTCCGGGGCC  ACGGCCACCG  CTGCCCTGCC

MOUSE CST   CCTGGAGAGT  GGCCCTACTG  GCCAGGACAG  ......TGTG  CAGGAAGCCA
RAT CST     CCTGGAGAGC  GGTCCCACCG  GCCAGGACAG  ......TGTG  CAGGATGCCA
HUMAN CST   CCTGGAGGGT  GGCCCCACCG  GCCGAGACAG  CGAGCATATG  CAGGAAGCGG

MOUSE CST   C...CGAGGG  GAGGAGCGGC  CTTCTGACTT  TCCTTGCCTG  GTGGCACGAG
RAT CST     CAGGCGGGAG  GAGGACCGGC  CTTCTGACTT  TCCTTGCCTG  GTGGCATGAG
HUMAN CST   CAGGAATAAG  GAAAAGCAGC  CTCCTGACTT  TCCTCGCTTG  GTGGTTTGAG

MOUSE CST   TGGGCTTCCC  AAGCCAGCTC  CAGCACCCCC  GTCGGAGGGG  GTACCCCCGG
RAT CST     TGGGCTTCCC  AAGACAGCTC  CAGCACCGCT  TTCGAAGGGG  GTACCCCGGA
HUMAN CST   TGGACCTCCC  AGGCCAGTGC  CGGGCCCCTC  ATAGGAGAGG  AAGCCCGGGA

MOUSE CST   GCTGTCCAAG  AGCCAGGAAA  GGCCACCCCC  CCAACAGCCC  CCACACCTGG
RAT CST     GCTGTCTAAG  CGGCAGGAAA  GACCACCCCT  CCAGCAGCCC  CCACACCGGG
HUMAN CST   GGTGGCCAGG  CGGCAGGAAG  GCGCACCCCC  CCAGCAATCC  GCGCGCCGGG

MOUSE CST   ATAAAAAGCC  CTGCAAGAAC  TTCTTCTGGA  AAACCTTCTC  CTCGTGCAAG
RAT CST     ATAAAAAGCC  CTGCAAGAAC  TTCTTCTGGA  AAACCTTCTC  CTCGTGCAAG
HUMAN CST   ACAGAATGCC  CTGCAGGAAC  TTCTTCTGGA  AGACCTTCTC  CTCCTGCAAA

MOUSE CST   TAACCCCACC  CTGGGCATAG  CACCCTGGCC  ACCCTGTGAG  ATGCCAACGA
RAT CST     TAGCCCGAGC  CTGACCGGAG  CCTGACCGGC  CACCCTGTGA  ATGCAGCCGT
HUMAN CST   TAAAACCTCA  CCCATGAATG  C.........  .TCACGCAAG  TGTAATGACA

MOUSE CST   GACCTGAATA  AAGACTGTCA  ATCAAC....  ..........  ..........
RAT CST     GGCCTGAATA  AAGAGTGTCA  AGT.......  ..........  ..........
HUMAN CST   GACCTGAATA  AAATGTATTA  AGCAGCAGTG  ATCTTTCCTC  TCCTCCTTCC

MOUSE CST   ..........  ..........  ..........  ..........  ..........
RAT CST     ..........  ..........  ..........  ..........  ..........
HUMAN CST   CAAGTCATTG  AAAAGTGTTT  GTTATTTAAA  TTCCAATAAT  GCCCAATACT

MOUSE CST   ..........  ..........  ..........  ..........  ..........
RAT CST     ..........  ..........  ..........  ..........  ..........
HUMAN CST   GACGTGTCTT  GAGTAATTTG  GAACCCAAAA  GTGAAGATCT  TGATAAAGA

MOUSE CST   ..........  ..........  ..........  ..........  ..........
RAT CST     ..........  ..........  ..........  ..........  ..........
HUMAN CST   TTTTTTTTGT  GGTTCGACTG  GACTGTGCTG  AGTGCGGGCA  CTGGGCTTTT

MOUSE CST   ..........  ..........  ..........  ..........  ..........
RAT CST     ..........  ..........  ..........  ..........  ..........
HUMAN CST   CTTCTGATGT  TCATTATGGT  GCTGGGAAGC  TCTGTCTTTG  ATTTAAAATA

MOUSE CST   ..........  .........
RAT CST     ..........  .........
HUMAN CST   AAATAGCTAA  AGGCTACAC
```

FIGURE 3a

|            | 1          |            |            |            | 50         |
|------------|------------|------------|------------|------------|------------|
| RAT CST    | .MGGCSTRGK | RPSALSLLLL | LLLSGIAASA | LPLESGPTGQ | DS..VQDATG |
| MOUSE CST  | MMGGRGTGGK | WPSAFGLLLL | W...GVAASA | LPLESGPTGQ | DS..VQEATE |
| HUMAN CST  | .......... | MPLSPGLLLL | LLSGATATAA | LPLEGGPTGR | DSEHMQEAAG |
| Consensus  | ---------- | -P----LLLL | ------A--A | LPLE-GPTG- | DS---Q-A-- |

|            | 51         |            |            |            | 100        |
|------------|------------|------------|------------|------------|------------|
| RAT CST    | GRRTGLLTFL | AWWHEWASQD | SSSTAFEGGT | PELSKRQERP | PLQQPPHRDK |
| MOUSE CST  | G.RSGLLTFL | AWWHEWASQA | SSSTPVGGGT | PGLSKSQERP | PPQQPPHLDK |
| HUMAN CST  | IRKSSLLTFL | AWWFEWTSQA | SAGPLIGEEA | REVARRQEGA | PPQQSARRDR |
| Consensus  | -----LLTFL | AWW-EW-SQ- | S--------- | ------QE-- | P-QQ----D- |

|            | 101        | 116        |
|------------|------------|------------|
| RAT CST    | KPCKNFFWKT | FSSCK      |
| MOUSE CST  | KPCKNFFWKT | FSSCK      |
| HUMAN CST  | MPCRNFFWKT | FSSCK      |
| Consensus  | -PC-NFFWKT | FSSCK      |

FIGURE 3b

6A
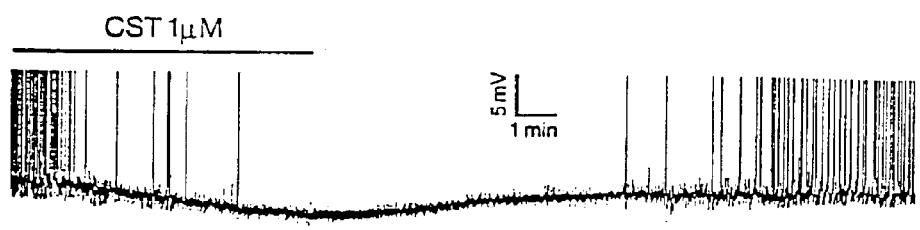
6B
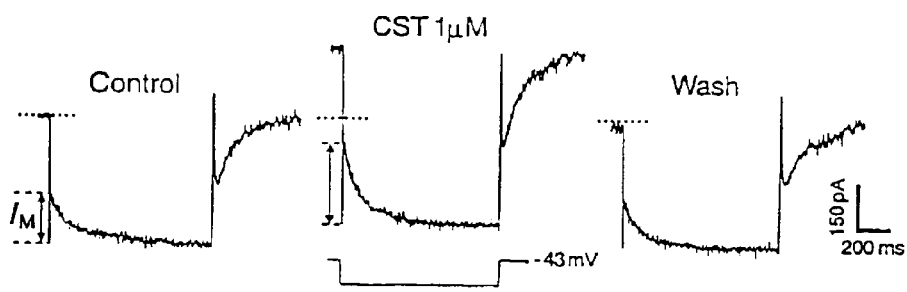
6C
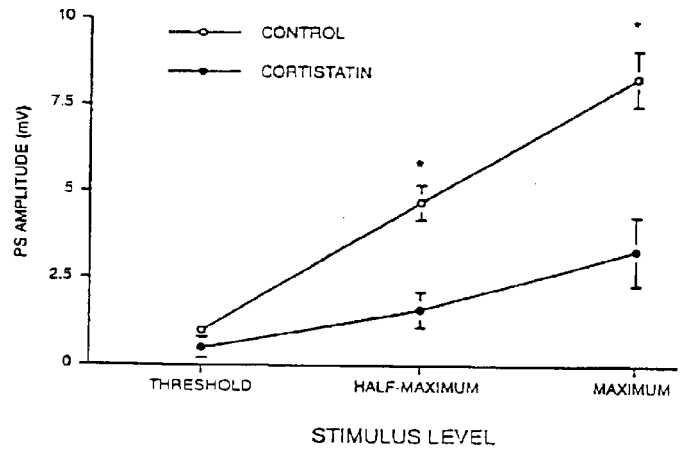
FIGURE 6

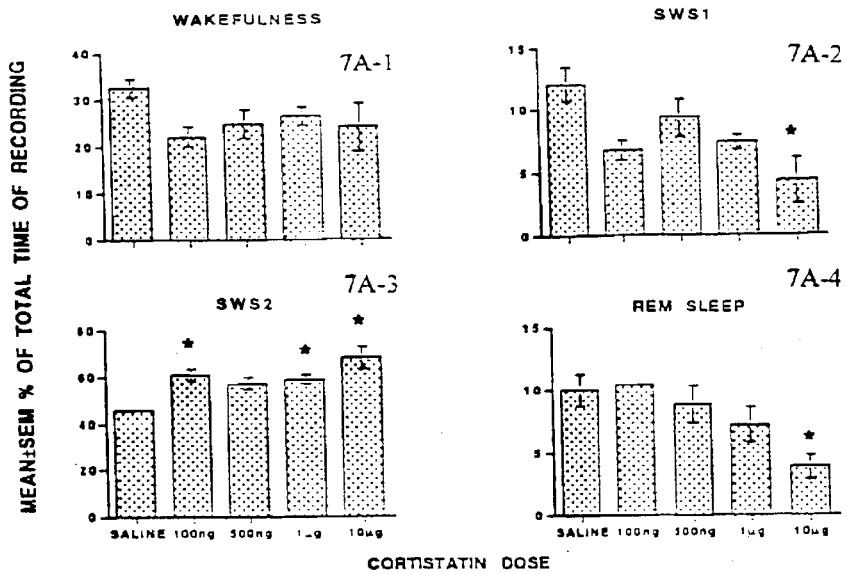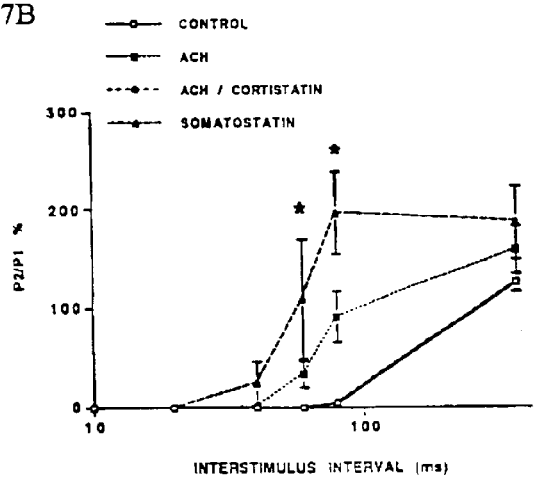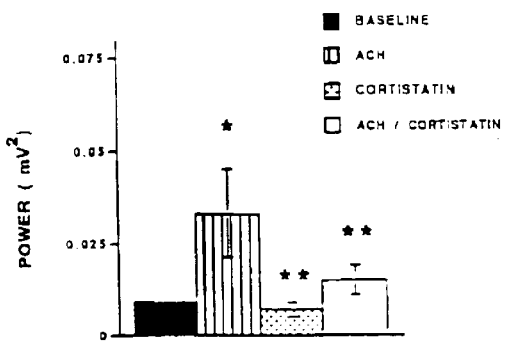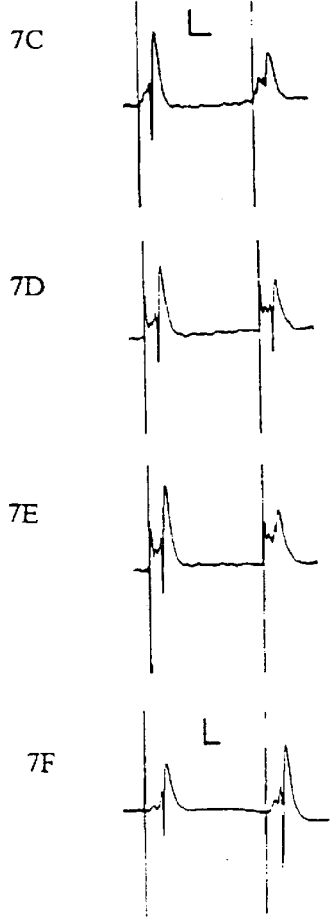
FIGURE 7

ANTIBODIES TO CORTISTATIN: NEUROPEPTIDES, COMPOSITIONS AND METHODS

CROSS REFERENCE TO RELATED APPLICATION

This application is a divisional application Ser. No. 08/857,389, filed May 15, 1997, now U.S. Pat. No. 6,479,642, which is incorporated herein by reference, which is a continuation-in-part of U.S. Ser. No. 08/648,322, filed May 15, 1996, now U.S. Pat. No. 6,074,872, the disclosure of which is incorporated by reference herein.

GOVERNMENT SUPPORT

This invention was made with the support of the United States Government and the United States Government has certain rights in the invention pursuant to the United States Public Health Service Contract GM32355 and NS22111.

TECHNICAL FIELD

The present invention relates generally to the discovery of a neuropeptide, designated cortistatin, that shares structural similarity with somatostatin yet, unlike somatostatin, enhances slow-wave sleep. Cortistatin nucleic acid and encoded polypeptides along with anti-cortistatin antibodies are useful in both screening methods, diagnostic methods and therapeutic methods related to modulation of sleep and disorders thereof.

BACKGROUND

Changes in arousal state from waking to sleep are accompanied by dramatic changes in the electroencephalogram (EEG). The low amplitude, high frequency pattern of the awake EEG becomes dominated by high amplitude, low frequency synchronized activity in slow-wave sleep (SWS), followed sequentially by rapid eye movement (REM) sleep (Steriade et al., Science, 262:679–685 (1993). Acetylcholine (ACh) plays a key role in the transition of the different phases of sleep (Shiromani et al., Ann. Rev. Pharmacol. Toxicol., 27:137–156 (1987). SWS requires low ACh levels whereas REM sleep is characterized by high ACh content. Also, these phases of sleep have been shown to be differentially sensitive to a number of endogenous neuropeptides and cytokines, including somatostatin, which is known to increase REM sleep without significantly affecting other phases (Borbely et al., Physiol. Rev., 69:605–670 (1989).

The present invention describes the cloning and characterization of cortistatin, a novel neuropeptide that has been discovered to be a sleep-modulating molecule with effects opposing those mediated by somatostatin. Cortistatin, however, exhibits strong structural similarity to somatostatin. Thus obtaining a cDNA clone from screening brain-specific libraries, the mRNA of which clone is translated into a naturally occurring physiologically active protein, is yet a further example of such molecules described in U.S. Pat. Nos. 4,900,811 and 5,242,798.

Although cortistatin has now been determined to be the product of a different gene, because of its structural similarity to somatostatin as well as functional aspects described herein, cortistatin is a new member of the somatostatin family whose distribution is primarily restricted to GABAergic cortical interneurons.

GABAergic neurons have been shown to finely modulate the output of principal neurons of the cerebral cortex and hippocampus (Buhl et al., Nature 368:823–828 (1994), areas that have been implicated in arousal state and complex cognitive functions, including learning and memory (Wilson et al., Science, 265:676–679 (1994).

The neuropeptide somatostatin was first described as a hypothalamic peptide that inhibited growth hormone release (Brazeau et al., Science, 179:77–79 (1973), and has since been implicated in many physiological phenomena, including hippocampal function and REM sleep generation (Danguir, Brain Res., 367:26–30 (1986). In the hippocampus, somatostatin is present largely in a particular set of interneurons. See, Hendry et al., Proc. Natl. Acad. Sci., USA, 81:6526–6530 (1984); Schemchel et al., Neurosci. Lett., 47:227–232 (1984); and Morrison et al., Brain Res., 262:344–351 (1983). Somatostatin may modulate the output of pyramidal neurons primarily by depressing neuronal excitability, in part via enhancement of the voltage-dependent potassium M current. See, Moore et al., Science, 239:278–280 (1988) and Schweitzer et al., Nature 346:464–466 (1990). Pharmacological studies have shown that somatostatin also interacts with cholinergic (Araujo et al., J. Neurochem., 55:1546–1555 (1990) and Mancillas et al., Proc. Natl, Acad. Sci., USA, 83:7518–7521 (1986) and GABAergic (Freund et al., Nature 336:170–173 (1988) systems, among others, thus modulating systems thought to underlie different aspects of behavior.

As shown in the present invention, despite the physical similarities between somatostatin and cortistatin, administration of cortistatin in vivo depresses neuronal electrical activity but, unlike somatostatin, induces low frequency waves in the cerebral cortex and antagonizes the effects of acetylcholine on hippocampal and cortical measures of excitability, thus providing a mechanism for cortical synchronization related to sleep.

BRIEF SUMMARY OF THE INVENTION

A mammalian neuropeptide, designated cortistatin, has now been discovered, cloned, sequenced and characterized for biological activity. Cortistatin is expressed in cortical and hippocampal mammalian interneurons, has an amino acid residue sequence similar to but distinct from somatostatin, and has neurologic properties including neuronal depression, sleep modulation and enhanced slow wave sleep.

The basic discovery of a new polypeptide of this nature provides a variety of embodiments, including compositions, methods of their use, and screening procedures for the identification of additional useful compositions.

In one embodiment, the invention describes a substantially isolated cortistatin protein and a cortistatin polypeptide including an amino acid residue sequence defining a cortistatin polypeptide having a sequence that corresponds to a sequence in the Sequence Listing selected from the group consisting of SEQ ID NOs 2, 5, 6, 7, 8, 9, 10, 11, 12, 23, 24, 26, positions 44 to 74 of SEQ ID NO 26, positions 77 to 105 of SEQ ID NO 26, and positions 89 to 105 of SEQ ID NO 26. The polypeptide can be synthetic, recombinant or a fusion protein. Polypeptide analogs of cortistatin are also described.

The invention also describes a substantially purified nucleic acid having a nucleotide sequence that encodes a cortistatin polypeptide having a sequence that corresponds to a sequence in the Sequence Listing selected from the group consisting of SEQ ID NOs 2, 5, 6, 7, 8, 9, 10, 11, 12, 23, 24, 26, positions 44 to 74 of SEQ ID NO 26, positions 77 to 105 of SEQ ID NO 26, and positions 89 to 105 of SEQ ID NO 26. The nucleic acid can be operatively linked to a promoter in an expression vector. Vectors for expressing cortistatin and cells containing the vectors are also described. Polynucleotide primers useful for hybridizing to cortistatin genes and gene products (e.g., mRNA) are also described.

The invention also contemplates an antibody that immunoreacts with cortistatin or with a polypeptide having a sequence that corresponds to a sequence in the Sequence Listing selected from the group consisting of SEQ ID NOs 2, 5, 6, 7, 8, 9, 10, 11, 12, 23, 24, 26, positions 44 to 74 of SEQ ID NO 26, positions 77 to 105 of SEQ ID NO 26, and positions 89 to 105 of SEQ ID NO 26. The antibody can also be a monoclonal antibody.

The invention also contemplates a kit for detecting the presence of cortistatin in a human body sample comprising an anti-cortistatin antibody, cortistatin polypeptide or oligonucleotide of the invention.

The invention further contemplates methods for detecting the presence of a nucleic acid that encodes cortistatin in a human body sample containing nucleic acid comprising the steps of:
(a) hybridizing the nucleic acid in the body sample with a oligonucleotide that includes at least 10 contiguous nucleotides from the nucleotide sequence shown in SEQ ID NO 1 from nucleotide 324 to nucleotide 366 to form a hybridization product; and
(b) detecting the presence of the hybridization product.

In a related method the invention describes a method of detecting the presence of a cortistatin antigen in a human body sample comprising the steps of:
(a) contacting a human body sample with an anti-cortistatin antibody that immunoreacts with human cortistatin or with a polypeptide having the amino acid residue sequence shown in SEQ ID NO 8 for a time period sufficient for said antibody to immunoreact with said antigen present in the sample and form an immunoreaction complex; and
(b) detecting the presence of an immunoreaction complex, thereby detecting said antigen.

Screening methods for identifying a ligand that binds to cortistatin receptor are also described which comprise:
(a) contacting a mammalian cell having a cortistatin receptor with a candidate ligand under conditions permitting binding of a known cortistatin receptor ligand to said cortistatin receptor; and
(b) detecting the presence of any of said candidate ligand bound to said receptor, or:
(a) contacting a mammalian cell having a cortistatin receptor with a candidate ligand under conditions permitting binding of a known cortistatin receptor ligand to said cortistatin receptor in the presence of a labeled cortistatin receptor ligand; and
(b) detecting the presence of any of said labeled ligand bound to said receptor.

Cortistatin polypeptides can also be used to directly detect the presence of a cortistatin receptor in a tissue sample comprising the steps of:
(a) contacting a tissue sample with an isolated cortistatin ligand under conditions permitting binding of a known cortistatin ligand to said cortistatin receptor; and
(b) detecting the presence of isolated cortistatin ligand bound to said tissue sample.

Therapeutic methods for altering cortistatin gene expression in a cell are contemplated comprising introducing into said cell an oligonucleotide capable of specifically hybridizing to the cortistatin gene. Alternatively, a method for activating the physiological response of cortistatin receptor upon binding to cortistatin is contemplated comprising contacting said cortistatin receptor with a pharmaceutical composition comprising a physiologically acceptable carrier and an effective activating amount of a cortistatin receptor agonist. Similarly, a cortistatin receptor antagonist can be used to inhibit the receptor.

Mutations in the cortistatin gene of a mammal that comprises an expansion of the CTG domain of the cortistatin gene can be assayed, comprising the steps of:
(a) determining the nucleotide sequence of the CTG domain of the cortistatin gene in a nucleic acid sample from said mammal; and
(b) comparing the determined nucleotide sequence to the known sequence of the CTG domain in a normal cortistatin gene to identify the presence of a sequence expansion in the CTG domain, and thereby said mutation.

The pharmacological activity of a cortistatin polypeptide can be exploited in a method for inducing sleep in a mammal comprising administering a physiologically tolerable composition containing a therapeutically effective amount of a cortistatin analog to said mammal. Similarly, sleep can be inhibited by use of a cortistatin receptor antagonist.

Other embodiments will be apparent to one skilled in the art.

BRIEF DESCRIPTION OF THE DRAWINGS

FIG. 1 illustrates the nucleotide sequence (SEQ ID NO: 1) and predicted amino acid sequence (SEQ ID NO: 2) of rat cortistatin as described in Example 1. The preprocortistatin cDNA clone displays a 336 nucleotide open reading frame with an N-terminal signal peptide whose cleavage site is indicated by an arrow. The CTG repeat contained within the coding region for the signal peptide is underlined. Two proteolytic cleavage sites (bold KK or KR) could give rise to peptides 13 (hatched lined box) and 14 amino acids long (solid lined box), or to the 29-residue precursor.

FIG. 2 illustrates the alignment of cortistatin-29 (CST) (SEQ ID NO: 2) and somatostatin-28 (SEQ ID NO: 3) amino acid sequences as described in Example 1.

FIG. 3 illustrates the nucleotide sequence (SEQ ID NO: 4) and predicted amino acid sequence (SEQ ID NO: 5) of mouse cortistatin as described in Example 1. The preprocortistatin cDNA clone displays a 327 nucleotide open reading frame with an N-terminal signal peptide whose cleavage site is indicated by an arrow. The CTG repeat contained within the coding region for the signal peptide is underlined. Two proteolytic cleavage sites (KS or KK) could give rise to a 13 amino acid peptide (hatched lined box) and a 14 amino acid peptide (solid lined box).

FIG. 3a illustrates the alignment of the nucleotide sequence of rat (SEQ ID NO: 1), mouse (SEQ ID NO: 4) and human (SEQ ID: 25) preprocortistatin cDNA. The human preprocortistatin cDNA displays a 315 nucleotide open reading frame. The CTG repeat that encodes the amino acid leucine, and that is of variable length between species has been underlined. Two possible polyadenylation signals are marked with an asterisk. Nucleotides conserved among all three species are shown in uppercase, and those not conserved are shown in lowercase.

FIG. 3b illustrates the alignment of the deduced amino acid sequences of the rat (SEQ ID NO: 2), mouse (SEQ ID NO: 5) and human (SEQ ID NO: 26) cortistatin precursors. The putative dibasic cleavage sites are indicated in bold.

Consensus residues are indicated. Proteolytic cleavage sites in human cortistatin (bold RR or RK) could give rise to a 31 amino acid peptide (hatched box), a 29 amino acid peptide, and a 17 amino acid peptide (solid box). lined box) and a 14 amino acid peptide (solid line box).

Figure 4:
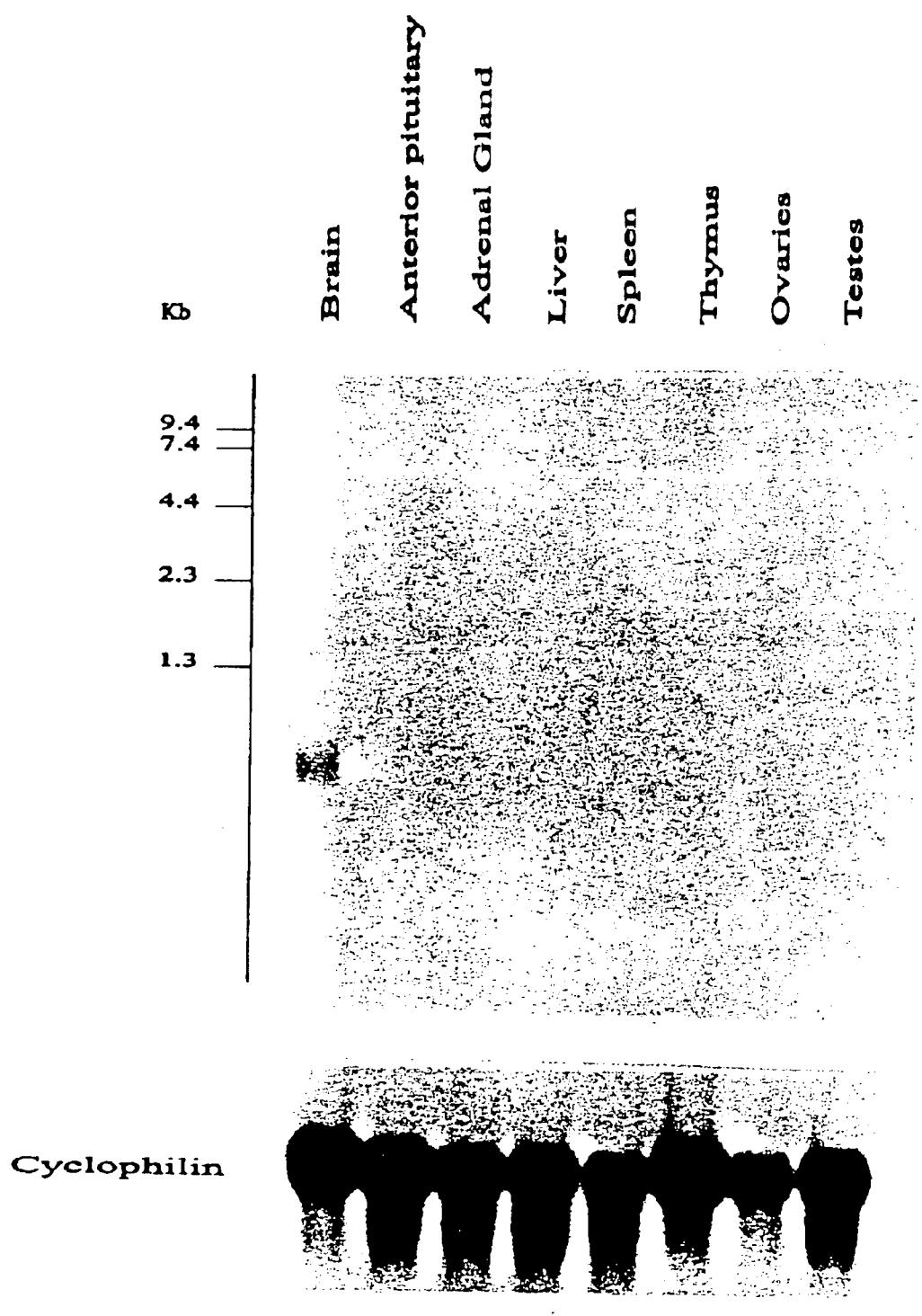

FIG. 4 illustrates a photograph of a Northern blot containing two micrograms of polyA+ selected RNA from rat brain, anterior pituitary, adrenal gland, liver, spleen, thymus, ovary and testes that was hybridized with a cortistatin cDNA probe as described in Example 4.

Figure 5:
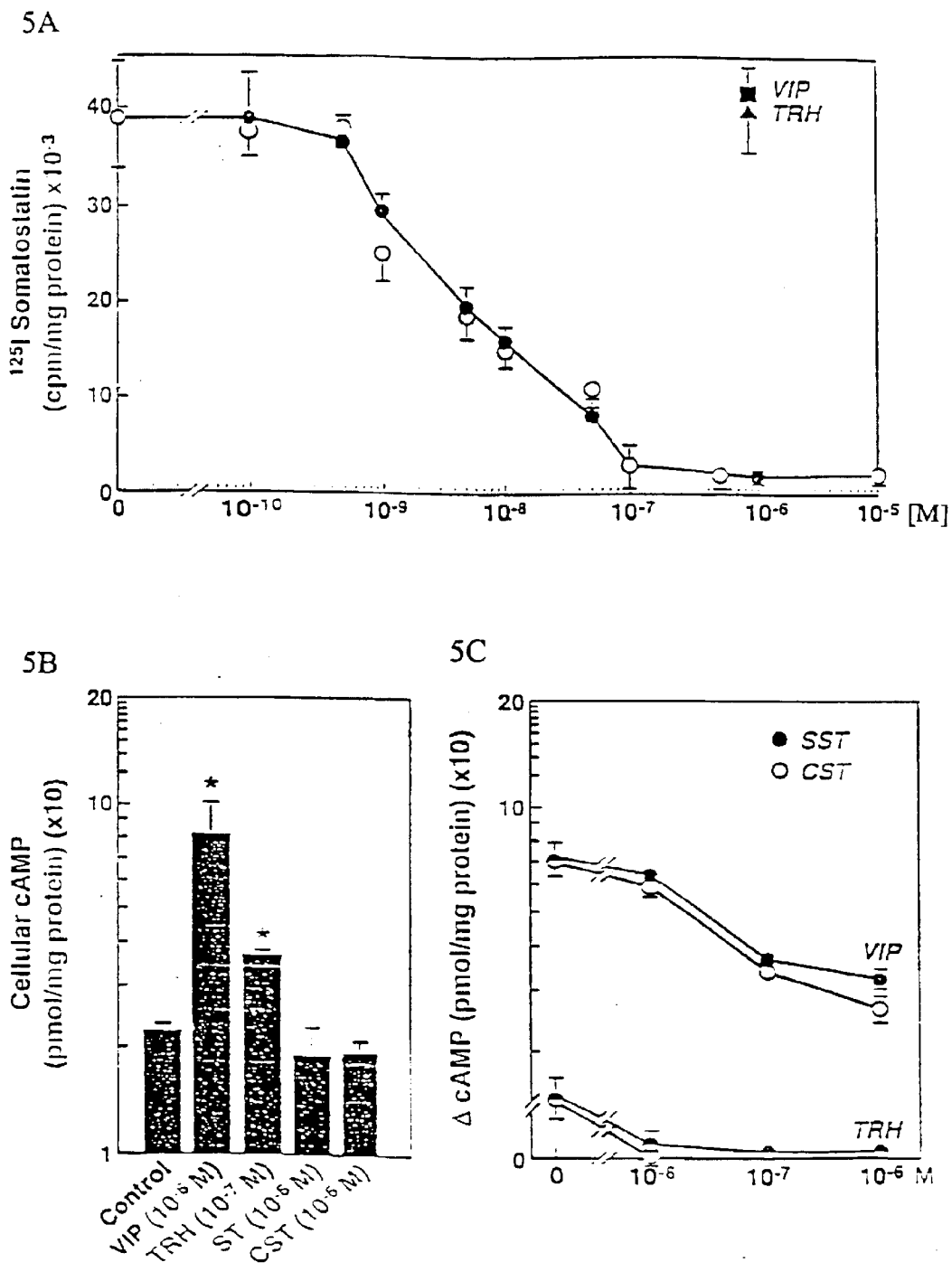

FIG. 5A illustrates the displacement of $^{125}$I-somatostatin bound to $GH_4$ pituitary cells by the peptides, somatostatin-14 and cortistatin-14, as described in Example 5. The displacement by cortistatin-14 is shown in the filled circles while that by somatostatin-14 is shown in the white circles. the counts per minute per milligram of iodinated somatostatin (cpm/mg protein)×$10^{-3}$ is listed on the Y-axis while the molarity (M) of the free peptides is listed on the X-axis. The combined data from four independent experiments are plotted as mean values Å standard error. Controls included TRH and VIP as described in Example 5.

FIG. 5B illustrates cyclic AMP stimulation in $GH_4$ cells following treatment with VIP, TRH, somatostatin-14 and cortistatin-14. The Y-axis plots the amount of intracellular CAMP levels in picomole per milligram of protein (pmol/mg protein)×10. The concentrations of the tested reagents are indicated on the X-axis. The results of the assay are discussed in Example 5.

FIG. 5C illustrates inhibition of stimulated CAMP levels by somatostatin-14 and cortistatin-14. The assay was performed as described in Example 5. On the Y-axis, the change of cAMP concentration in pmol/mg protein×10 is indicated against the concentration of the peptides for either VIP or TRH induction on the X-axis. Each data point represents 2–4 replicates and the experiments were carried out twice.

FIG. 6A illustrates the current-clamp recording of a CA1 neuron manually depolarized to −65 mV (resting membrane potential was −70 mV) to elicit action potential firing (upward deflections, truncated) by superfusion with 1 M cortistatin-14 (bar above record). The assay and results are discussed in Example 8.

FIG. 6B illustrates voltage-clamp recording of a CA1 neuron held at −43 mV following treatment with cortistatin at 1 M for 7 minutes; an $I_M$ relaxation was evoked with 10 mV hyperpolarizing step. Arrows indicate the $I_M$ relaxation amplitude while the dotted lines indicate an outward steady-state control holding current. The assay and results are discussed in Example 8.

FIG. 6C illustrates the effects of cortistatin-14 on population spike (PS) amplitudes in CA1 neurons in vivo. The assays and results are discussed in Example 8. Stimulus response curves are indicated with the PS amplitude plotted on the Y-axis in mV against the stimulus level plotted on the X-axis at three response levels: threshold, half-maximal and maximal (control mean half-maximal PS amplitude=4.7 mV Å 0.5; n=5).

FIGS. 7A-1 through 7A-4 illustrate the effect of the intracerebroventricular administration of cortistatin-14 on the sleep-wake cycle of the rat. FIGS. 7A-1, 7A-2, 7A-3 and 7A-4 respectively show wakefulness, slow-wave sleep 1 (SWS1), slow-wave sleep 2 (SWS2) and rapid eye movement (REM) sleep. The graphs all have the mean +/− the standard error of the mean percent (%) of total time of the recording plotted on the Y-axis against the varying amount of cortistatin-14 or control plotted on the X-axis. The assay and results are discussed in Example 8.

FIG. 7B illustrates the effects of iontophoretically applied acetylcholine (ACh) (0.9 M), somatostatin-14 (1.5 mM) and cortistatin-14 on PP responses in CA1 neurons in vivo. The percent of P2/P1 response is plotted on the Y-axis against the interstimulus interval in milliseconds (ms) plotted on the X-axis. The control is plotted with a empty circle while that with ACh is indicated with a dashed line and a filled square. The results with somatostatin-14 are indicated with a dashed line marked with an open triangle and the combined ACh/cortistatin-14 treatment is indicated with a dashed line marked with a filled circle. The assay and results are discussed in Example 8.

FIGS. 7C through 7F representative recordings of field potentials elicited in CA1 by commissural stimulation in 80 millisecond intervals. The baseline recording is plotted in FIG. 7C with the calibration bars of 2 mV and 10 ms. FIG. 7D shows the reduction of PP inhibition with iontophoretic administration of ACH. FIG. 7E shows that simultaneous application of cortistatin-14 with ACH antagonized the effect seen in FIG. 7D. FIG. 7F shows decreased PP inhibition obtained with somatostatin-14 (calibration bars of 1 mV and 10 ms). The assay and results are discussed in Example 8.

FIG. 7G illustrates the effects of microiontophoretically (100–250 nA) applied ACH and cortistatin-14 on local EEG activity recorded in the visual cortex. The assay and results are discussed in Example 8. The averaged/EEG power spectra is plotted on the Y-axis in mV2 against fast activity of responses in baseline (filled column), ACH treatment (vertical lined-column), cortistatin-14 (dotted column) and ACH/cortistatin-14 treated (empty column). The assay and results are discussed in Example 8.

DETAILED DESCRIPTION OF THE INVENTION

A. Definitions

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552–59 (1969) and adopted at 37 CFR §1.822(b)(2)), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |

-continued

TABLE OF CORRESPONDENCE

| SYMBOL | | |
|---|---|---|
| 1-Letter | 3-Letter | AMINO ACID |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left-to-right orientation in the conventional direction of amino terminus to carboxy terminus. In addition, the phrase "amino acid residue" is broadly defined to include the amino acids listed in the Table of Correspondence and modified and unusual amino acids, such as those listed in 37 CFR 1.822(b)(4), and incorporated herein by reference. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

Recombinant DNA (rDNA) Molecule: a DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evolutionarily different, are said to be "heterologous".

Vector: a rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors".

Receptor: A receptor is a molecule, such as a protein, glycoprotein and the like, that can specifically (non-randomly) bind to another molecule.

Antibody: The term antibody in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab')$_2$ and F(v).

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof.

Monoclonal Antibody: A monoclonal antibody in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody. Although historically a monoclonal antibody was produced by immortalization of a clonally pure immunoglobulin secreting cell line, a monoclonally pure population of antibody molecules can also be prepared by the methods of the present invention.

Upstream: In the direction opposite to the direction of DNA transcription, and therefore going from 5' to 3' on the non-coding strand, or 3' to 5' on the mRNA.

Downstream: Further along a DNA sequence in the direction of sequence transcription or read out, that is traveling in a 3'- to 5'-direction along the non-coding strand of the DNA or 5'- to 3'-direction along the RNA transcript.

Reading Frame: Particular sequence of contiguous nucleotide triplets (codons) employed in translation that define the structural protein encoding-portion of a gene, or structural gene. The reading frame depends on the location of the translation initiation codon.

Polypeptide: A linear series of amino acid residues connected to one another by peptide bonds between the alpha-amino group and carboxy group of contiguous amino acid residues.

Protein: A linear series of greater than 50 amino acid residues connected one to the other as in a polypeptide.

Substantially Purified or Isolated: When used in the context of polypeptides or proteins, the terms describe those molecules that have been separated from components that naturally accompany them. Typically, a monomeric protein is substantially pure when at least about 60% to 75% of a sample exhibits a single polypeptide backbone. Minor variants or chemical modifications typically share the same polypeptide sequence. A substantially purified protein will typically comprise over about 85% to 90% of a protein sample, more usually about 95%, and preferably will be over about 99% pure. Protein or polypeptide purity or homogeneity may be indicated by a number of means well known in the art, such as polyacrylamide gel electrophoresis of a sample, followed by visualization thereof by staining. For certain purposes, high resolution is needed and high performance liquid chromatography (HPLC) or a similar means for purification utilized.

Synthetic Peptide: A chemically produced chain of amino acid residues linked together by peptide bonds that is free of naturally occurring proteins and fragments thereof.

B. Cortistatin Proteins and Polypeptides

Cortistatin has been cloned, sequenced and characterized from a variety of mammalian species, indicating that it is a neuropeptide found in all mammals, including humans, rodents, mice, and the like mammals. The neuropeptide is not identical in amino acid residue sequence between mammalian species, but is sufficiently similar that allows generalizations regarding function, and assures that one can identify and isolate the cortistatin gene in any mammalian species.

Thus, variations at both the amino acid and nucleotide sequence level are described in isolates of cortistatin, and such variations are not to be construed as limiting. For example, allelic variation within a mammalian species can tolerate a several percent difference between isolates of a type of cortistatin, which differences comprise non-deleterious variant amino acid residues. Thus a protein of about 95% homology, and preferably at least 98% homology, to a disclosed cortistatin is considered to be an allelic variant of the disclosed cortistatin, and therefore is considered to be a cortistatin of this invention.

As disclosed herein, cortistatin is produced first in vivo in precursor form, and is then processed into smaller polypeptides having biological activity as described herein. Insofar as these different polypeptide forms are contemplated as useful, the term cortistatin protein or polypeptide connotes all species of polypeptide having an amino acid residue sequence derived from the cortistatin gene.

The complete coding nucleotide sequence of rat preprocortistatin cDNA is 438 nucleotides in length as shown in FIG. 1 and listed in SEQ ID NO 1. The complete preprocortistatin cDNA clone presents a 336 nucleotide open reading frame (ORF) with a N-terminal signal peptide whose cleavage site between amino acid positions 27 and 28 corresponding to a cleavage site after nucleotide position 110.

Translation of this rat cDNA sequence encodes that a novel protein of 112 amino acid residues, referred to as rat preprocortistatin. The amino acid sequence of rat preprocortistatin is also listed in SEQ ID NO 1 with the nucleotide sequence and in SEQ ID NO 2 alone.

Cleavage of the preprospecies to rat procortistatin produces a mature protein that is processed at either of two tandem basic amino acid pairs, KK (lys-lys) or KR (lys-arg) to produce mature cortistatin proteins referred to as cortistatin-29 and cortistatin-14. This cleavage pattern is analogous to the cleavage of preprosomatostatin at 28 and 14 residues as described by Glushankov et al., *Proc Natl. Acad. Sci., USA*, 81:6662–6666 (1984). Alternatively, cleavage at both basic pairs results in the production of mature cortistatin-13 in addition to cortistatin-14. The rat preprospecies along with prospecies and mature cleavage products are listed in the Examples in Table 1 including their noted amino acid residue sequences.

Although cortistatin-13 is unrelated to known species, cortistatin-14 shares 11 of 14 residues with somatostatin-14 as discussed in Example 1.

Thus, the noted nucleotide and amino acid differences between somatostatin and cortistatin indicate clearly that they are the products of separate genes.

The mouse homolog to the rat preprocortistatin cDNA has a complete coding nucleotide sequence of 427 nucleotides in length, as shown in FIG. 3 and listed in SEQ ID NO 4. The complete preprocortistatin cDNA clone presents a 327 nucleotide open reading frame (ORF) with a N-terminal signal peptide whose cleavage site is between amino acid positions 25 and 26 corresponding to a cleavage site after nucleotide position 99.

Translation of this mouse cDNA sequence provides a novel protein of 109 amino acid residues, provisionally called mouse preprocortistatin. The amino acid sequence of mouse preprocortistatin is listed in SEQ ID NO 4 with the nucleotide sequence and in SEQ ID NO 5 alone.

Similar to the rat preprocortistatin, cleavage of the mouse preprospecies to procortistatin generates a mature protein that is processed at either of two tandem basic amino acid pairs, KS (lys-ser) and KK (lys-lys), to produce mouse cortistatin-29 and mouse cortistatin-14. As with the rat cleavage patterns, two smaller mouse cortistatin species of 13 and 14 amino acid residues are produced when cleavage occurs at both sets of basic residues. The mouse preprospecies along with the prospecies and the mature proteins are listed in Table 1 in the Examples including their noted amino acid residue sequences.

By introducing two gaps, the mouse and rat nucleotide sequences are 86% identical. Assuming that the mouse translation initiation product begins at the second methionine triplet, it contains 108 amino acids compared to 112 for rat. Again, after introduction of two gaps, the rat and mouse proteins share 82% identity. The mouse nucleotide sequence corresponding to cortistatin-14 and the adjacent lysine doublet that serves as its site of proteolytic release from its precursor were identical to same region in the rat sequence, thus supporting a functional conservation of the mature peptide. The DNA sequence upstream from the processing site of cortistatin 14 showed several points of divergence, including some resulting in non-conservative amino acid substitutions.

In view of the conserved domains and cleavage sites for generating mature cortistatin proteins for two mammals, rats and mice, similar cleavage patterns and resultant protein species are identifiable in other mammals including humans.

The human homolog to the rat preprocortistatin cDNA has a complete coding nucleotide sequence of 701 nucleotides in length, as shown in FIG. 3a and listed in SEQ ID NO 25. The complete preprocortistatin cDNA clone presents a 315 nucleotide open reading frame, beginning at position 78 of SEQ ID NO 25.

Translation of this human cDNA sequence provides a novel protein of 105 amino acid residues, provisionally called human preprocortistatin. The amino acid sequence of human preprocortistatin is shown in FIG. 3b, and listed in SEQ ID NO 26.

Similar to the rat preprocortistatin, cleavage of the human preprospecies to procortistatin generates a mature protein that is processed at either of two RR (arg-arg) tandem basic amino acid pairs, to produce human cortistatin-29 (positions 77 to 105 of SEQ ID NO. 26) and human cortistatin-17 (positions 89 to 105 of SEQ ID NO 26). The human preprospecies along with the prospecies and the mature proteins are listed in Table 1 in the Examples including their noted amino acid residue sequences.

The human and rat nucleotide sequences are 71-identical. The human cortistatin-17 shares 13 of the last 14 residues with rat and mouse cortistatin-14. The lysine doublet that lies just N-terminal to cortistatin-14 in the rat and mouse is not conserved in the human sequence. The DNA sequence upstream from the processing site of cortistatin-14 are not very conserved across species. However, rat cortistatin-31 and human cortistatin-31 (positions 44 to 74 of SEQ ID NO 26) share 13 residues clustered in their N-terminal regions that are conserved among the rat, mouse, and human prohormone sequences.

A cortistatin protein of this invention can be in a variety of forms, depending upon the use therefor, as described herein. For example, a cortistatin can be isolated from a natural tissue.

Alternatively, a cortistatin of this invention can be recombinant protein, that is, produced by recombinant DNA (rDNA) methods as described herein. A recombinant cortistatin protein need not necessarily be substantially pure, or even isolated, to be useful in certain embodiments, although recombinant production methods are a preferred means to produce a source for further purification to yield an isolated or substantially pure receptor composition. A recombinant cortistatin protein can be present in or on a mammalian cell line or in crude extracts of a mammalian cell line.

In one embodiment, a cortistatin protein is substantially free of other neuropeptides, so that the purity of a cortistatin reagent and freedom from pharmacologically distinct proteins affords use in the screening methods. The recombinant production methods are ideally suited to produce absolute purity in this regard, although biochemical purification methods from natural sources are also contemplated. In this regard, a cortistatin protein is substantially free from other neuropeptides if there are insufficient other neuropeptides such that pharmacological cross-reactivity is not detected in conventional screening assays for ligand binding or biological activity.

Preferably, a cortistatin protein of this invention is present in a composition in an isolated form, i.e., comprising at least about 0.1 percent by weight of the total composition, preferably at least 1%, and more preferably at least about 90%. Particularly preferred is a substantially pure preparation of cortistatin, that is at least 90% by weight, and more preferably at least 99% by weight. Biochemical methods useful for the enrichment and preparation of an isolated cortistatin based on the chemical properties of a polypeptide are well known, and can be routinely used for the production of proteins which are enriched by greater than 99% by weight.

An isolated or recombinant cortistatin protein of this invention can be used for a variety of purposes, as described further herein. A cortistatin protein can be used as an immunogen to produce antibodies immunoreactive with cortistatin. Cortistatin proteins can be used in in vitro ligand binding assays for identifying ligand binding specificities, and agonists or antagonists thereto, to characterize candidate pharmaceutical compounds useful for modulating cortistatin function, and as therapeutic agents for effecting cortistatin functions. Other uses will be readily apparent to one skilled in the art.

Furthermore, the invention contemplates analogs of a cortistatin protein of this invention. An analog is a man-made variant which exhibits the qualities of a cortistatin of this invention in terms of immunological reactivity, ligand binding capacity or the like functional properties of a cortistatin protein of this invention. An analog can therefore be a cleavage product of cortistatin, can be a polypeptide corresponding to a portion of cortistatin, can be cortistatin polypeptide in which a membrane anchor has been removed, and can be a variant cortistatin sequence in which some amino acid residues have been altered, to name a few permutations.

Insofar as the present disclosure identifies cortistatin from different mammalian species, the present invention is not to be limited to a cortistatin protein derived from one or a few mammalian species. Thus, the invention contemplates a mammalian cortistatin protein, which can be derived, by rDNA or biochemical purification from natural sources, from any of a variety of species including man, mouse, rabbit, rat, dog, cat, sheep, cow, and the like mammalian species, without limitation. Human and agriculturally relevant animal species are particularly preferred.

Exemplary cortistatin species identified herein are mouse, rat and human cortistatin.

The nucleotide (cDNA) sequence of rat preprocortistatin is shown in SEQ ID NO 1, and corresponding amino acid residue sequence of rat preprocortistatin is shown in SEQ ID NO 2. The amino acid residue sequence of rat procortistatin is shown in SEQ ID NO 6, and cleavage products are shown in SEQ ID NOs 7, 8 and 9.

The nucleotide (cDNA) sequence of mouse preprocortistatin is shown in SEQ ID NO 4, and corresponding amino acid residue sequence of mouse preprocortistatin is shown in SEQ ID NO 5. The amino acid residue sequence of mouse procortistatin is shown in SEQ ID NO 10, and cleavage products are shown in SEQ ID NOs 8, 11 and 12.

The nucleotide (cDNA) sequence of human preprocortistatin is shown in SEQ ID NO 25, and corresponding amino acid residue sequence of human preprocortistatin is shown in SEQ ID NO 26. The amino acid residue sequences of the cleavage products are located at positions 44 to 74 (human cortistatin-31), positions 77 to 105 (human cortistatin-29), and positions 89 to 105 (human cortistatin-17) of SEQ ID NO 26. The peptide designated rat cortistatin-14 is highly conserved among species, and is identical in sequence between mouse and rat and shares 13 of the last 14 residues with human cortistatin-17. The amino acid residue sequence of mouse and rat cortistatin-14 is shown in SEQ ID No 8, and the amino acid residue sequence of human cortistatin-17 is shown in positions 89 to 105 of SEQ ID NO 26.

A cortistatin protein of this invention can be prepared by a variety of means, although expression in a mammalian cell using a rDNA expression vector is preferred. Exemplary production methods for a recombinant cortistatin are described in the Examples.

Thus, the invention also provides a method for the production of isolated cortistatin proteins, either as intact cortistatin protein, as fusion proteins or as smaller polypeptide fragments of cortistatin. The production method generally involves inducing cells to express a cortistatin protein of this invention, recovering the cortistatin from the resulting cells, and purifying the cortistatin so recovered by biochemical fractionation methods, using a specific antibody of this invention, or other chemical procedures.

The inducing step can comprise inserting a rDNA vector encoding a cortistatin protein, or fragment thereof, of this invention, which rDNA is capable of expressing a cortistatin, into a suitable host cell, and expressing the vector's cortistatin gene.

As used herein, the phrase "cortistatin polypeptide" refers to a polypeptide having an amino acid residue sequence that comprises an amino acid residue sequence that corresponds, and preferably is identical, to a portion of a cortistatin of this invention.

A cortistatin polypeptide of the present invention has a variety of uses according to the present invention.

Thus, a cortistatin polypeptide of this invention is characterized by its ability to immunologically mimic an epitope (antigenic determinant) expressed by a cortistatin of this invention. Such a polypeptide is useful herein as a component in an inoculum for producing antibodies that immunoreact with native cortistatin and as an antigen in immunologic methods. Representative and preferred cortistatin polypeptides for use as an immunogen in an inoculum are shown herein.

As used herein, the phrase "immunologically mimic" in its various grammatical forms refers to the ability of a cortistatin polypeptide of this invention to immunoreact with an antibody of the present invention that recognizes a conserved native epitope of a cortistatin as defined herein.

It should be understood that a subject polypeptide need not be identical to the amino acid residue sequence of a cortistatin receptor, so long as it includes the required sequence.

In addition, certain cortistatin polypeptides derived from receptor binding portions of cortistatin have the capacity to inhibit the binding of the cortistatin that would normally bind a cortistatin receptor. Thus, the invention also contemplates cortistatin polypeptides which are specifically designed for their capacity to mimic exposed regions of cortistatin involved in cortistatin receptor binding interactions and thereby receptor function. Therefore, these polypeptides have the capacity to function as analogs to cortistatin, and thereby block function. Such inhibitors of binding are referred to as therapeutic polypeptides because of their inhibitory capacity.

In addition, polypeptides corresponding to exposed domains have the ability to induce antibody molecules that immunoreact with a cortistatin of this invention at portions of cortistatin involved in receptor protein function, and therefor the antibodies are also useful at modulating normal cortistatin function.

A cortistatin polypeptide is preferably no more than about 120 amino acid residues in length for reasons of ease of synthesis. Thus, it more preferred that a cortistatin polypeptide be no more that about 100 amino acid residues, still more preferably no more than about 50 residues, and most preferably less than 30 amino acid residues in length when synthetic methods of production are used.

Thus, the present invention also contemplates a cortistatin polypeptide that has an amino acid residue sequence that corresponds to the sequence of the cortistatin protein shown in the sequence listings, and includes an amino acid residue sequence represented by a formula selected from the group consisting of the polypeptides shown in the sequence listings. In this embodiment, the polypeptide is further characterized as having the ability to mimic a cortistatin epitope and thereby inhibits cortistatin function in a classic cortistatin receptor activation assay, as described herein.

Due to the three dimensional structure of a native folded cortistatin molecule, the present invention contemplates that multiple regions of cortistatin are involved in cortistatin receptor function, which multiple and various regions are defined by the various cortistatin polypeptides described above. The ability of the above-described polypeptides to inhibit receptor-ligand binding can readily be measured in a ligand binding assay as is shown in the Examples herein. Similarly, the ability of the above-described polypeptides to inhibit cortistatin receptor function can readily be measured in a receptor assay as is described herein.

Thus, in another embodiment, the invention contemplates cortistatin polypeptide compositions that comprise one or more of the different cortistatin polypeptides described above which inhibit cortistatin receptor function, admixed in combinations to provide simultaneous inhibition of multiple contact sites on the cortistatin receptor.

A subject polypeptide includes any analog, fragment or chemical derivative of a polypeptide whose amino acid residue sequence is shown herein so long as the polypeptide is capable of mimicking an epitope of cortistatin. Therefore, a present polypeptide can be subject to various changes, substitutions, insertions, and deletions where such changes provide for certain advantages in its use. In this regard, a cortistatin polypeptide of this invention corresponds to, rather than is identical to, the sequence of a cortistatin protein where one or more changes are made and it retains the ability to induce antibodies that immunoreact with a cortistatin of this invention.

The term "analog" includes any polypeptide having an amino acid residue sequence substantially identical to a sequence specifically shown herein in which one or more residues have been conservatively substituted with a functionally similar residue and which displays the ability to induce antibody production as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. D-amino acids may also be included in place of one or more L-amino acids. Polypeptides of the present invention also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

When a polypeptide of the present invention has a sequence that is not identical to the sequence of a cortistatin polypeptide, it is typically because one or more conservative or non-conservative substitutions have been made, usually no more than about 30 number percent, more usually no more than 20 number percent, and preferably no more than 10 number percent of the amino acid residues are substituted. Additional residues may also be added at either terminus for the purpose of providing a "linker" by which the polypeptides of this invention can be conveniently affixed to a label or solid matrix, or carrier. Preferably the linker residues do not form a cortistatin epitope, i.e., are not similar is structure to a cortistatin protein.

Labels, solid matrices and carriers that can be used with the polypeptides of this invention are described hereinbelow.

Amino acid residue linkers are usually at least one residue and can be 40 or more residues, more often 1 to 10 residues, but do not form a cortistatin epitope. Typical amino acid residues used for linking are tyrosine, cysteine, lysine, glutamic and aspartic acid, or the like. In addition, a subject polypeptide can differ, unless otherwise specified, from the natural sequence of a cortistatin protein by the sequence being modified by terminal-NH₂ acylation, e.g., acetylation, or thioglycolic acid amidation, by terminal-carboxlyamidation, e.g., with ammonia, methylamine, and the like.

When coupled to a carrier to form what is known in the art as a carrier-hapten conjugate, a cortistatin polypeptide of the present invention is capable of inducing antibodies that immunoreact with cortistatin. In view of the well established principle of immunologic cross-reactivity, the present invention therefore contemplates antigenically related variants of the polypeptides shown herein. An "antigenically related variant" is a subject polypeptide that is capable of inducing antibody molecules that immunoreact with a polypeptide described herein and with a cortistatin protein of this invention.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di-and tri-alkyl and aryl amines (e.g. triethylamine, diisopropyl amine, methyl amine, dimethyl amine and the like) and optionally substituted ethanolamines (e.g. ethanolamine, diethanolamine and the like).

A cortistatin polypeptide of the present invention, also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in J. M. Steward and J. D. Young, "Solid Phase Peptide Synthesis", W. H. Freeman Co., San Francisco, 1969; M. Bodanszky, et al., "Peptide Synthesis", John Wiley & Sons, Second Edition, 1976 and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis, each of which is incorporated herein by reference. Additional peptide synthesis methods are described by Sutcliffe in U.S. Pat. Nos. 4,900,811 and 5,242,798, which are hereby incorporated by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final polypeptide.

A cortistatin polypeptide can be used, inter alia, in the diagnostic methods and systems of the present invention to detect a cortistatin receptor or cortistatin itself present in a body sample, or can be used to prepare an inoculum as described herein for the preparation of antibodies that immunoreact with conserved epitopes on cortistatin.

In addition, certain of the cortistatin polypeptides of this invention can be used in the therapeutic methods of the present invention to inhibit cortistatin function as described further herein.

C. Nucleic Acids and Polynucleotides

The DNA segments of the present invention are characterized as including a DNA sequence that encodes a cortistatin protein of this invention. That is, the DNA segments of the present invention are characterized by the presence of some or all of a cortistatin structural gene. Preferably the gene is present as an uninterrupted linear series of codons where each codon codes for an amino acid residue found in the cortistatin protein, i.e., a gene free of introns.

One preferred embodiment is a DNA segment that codes an amino acid residue sequence that defines a cortistatin protein as defined herein, and the DNA segment is capable of expressing a cortistatin protein of this invention. A preferred DNA segment codes for an amino acid residue sequence substantially the same as, and preferably consisting essentially of, an amino acid residue sequence shown in the sequence listing for a cortistatin protein, such as in SEQ ID NOs 2, 5, 6, 7, 8, 9, 10, 11, 12, 26, positions 44 to 74 of SEQ ID NO 26, positions 77 to 105 of SEQ ID NO 26, and positions 89 to 105 of SEQ ID NO 26. Particularly preferred DNA segments have a nucleotide sequence derived from the sequence shown in SEQ ID NOs 1 ,4 or 25. Representative and preferred DNA segments are described in the Examples.

Homologous DNA and RNA sequences that encode the above cortistatin protein are also contemplated.

The amino acid residue sequence of a protein or polypeptide is directly related via the genetic code to the deoxyribonucleic acid (DNA) sequence of the structural gene that codes for the protein. Thus, a structural gene or DNA segment can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences may code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

A nucleic acid is any polynucleotide or nucleic acid fragment, whether it be a polyribonucleotide of polydeoxyribonucleotide, i.e., RNA or DNA, or analogs thereof. In preferred embodiments, a nucleic acid molecule is in the form of a segment of duplex DNA, i.e, a DNA segment, although for certain molecular biological methodologies, single-stranded DNA or RNA is preferred.

DNA segments (i.e., synthetic oligonucleotides) that encode portions of cortistatin proteins can easily be synthesized by chemical techniques, for example, the phosphotriester method of Matteucci, et al., (*J. Am. Chem. Soc.*, 103:3185–3191, 1981) or using automated synthesis methods. In addition, larger DNA segments can readily be prepared by well known methods, such as synthesis of a group of oligonucleotides that define the DNA segment, followed by hybridization and ligation of oligonucleotides to build the complete segment.

Of course, by chemically synthesizing the coding sequence, any desired modifications can be made simply by substituting the appropriate bases for those encoding the native amino acid residue sequence.

Furthermore, DNA segments consisting essentially of structural genes encoding a cortistatin protein can be obtained from recombinant DNA molecules containing a gene that defines a cortistatin protein of this invention, and can be subsequently modified, as by site directed mutagenesis, to introduce any desired substitutions.

1. Cloning Cortistatin Genes

Cortistatin genes of this invention can be cloned by a variety of cloning methods and from any mammalian species. The cloning is based on the observation that there is a significant degree of homology between mammalian species for any given cortistatin of this invention, and therefor can be conducted according to the general methods described in the Examples, using nucleic acid homology strategies.

A typical degree of homology required to successfully clone a cortistatin is at least about 80% homologous at the DNA level, and at least about 90% homologous at the protein level. Preferred cloning strategies for isolating a nucleic acid molecule that encodes a cortistatin molecule of this invention are described in the Examples, and includes the recitation of polynucleotide probes useful for the screening of libraries of nucleic acid molecules believed to contain a target cortistatin gene. Particularly preferred probes encode the conserved region defined by "cortistatin-14" as described herein.

Sources of libraries for cloning a cortistatin gene of this invention can include genomic DNA or messenger RNA (mRNA) in the form of a cDNA library from a tissue believed to express a cortistatin of this invention. Preferred tissues are brain tissues, particularly cerebral cortex or hippocampal tissue.

The similarities between rat and mouse cortistatin are further extended to the identification of a sequence of iteration of trinucleotide CTG repeats. For the rat, a sequence of six iterations of the trinucleotide CTG repeats is present encoding leucine residues. In the mouse, a sequence of three iterations of the trinucleotide CTG is present, also within the region encoding the signal sequence. Thus, the presence of the iterations is typically located within the coding region for the signal peptide.

Such a triplet expansion in other genes has been implicated as causal in neurological diseases, e.g., myotonic dystrophy as described by Brook et al., *Cell*, 68:799–808 (1992) and fragile-X syndrome as described by Fu et al., *Cell*, 67:1047–1058 (1991). In myotonic dystrophy patients who are mildly affected, at least 50 CTG repeats are present. In severely affected individuals, the expansion can exist up to several kilobase pairs. In contrast, in the normal population, the repeat sequence is highly variable ranging from 5 to 27 copies. Individuals with varying severities of fragile-X have been similarly characterized.

Thus, screening for the presence of a region of DNA in which the repeats are present in either normal, underexpansion or overexpansion form can provide a genetic basis for diagnosis for some diseases. The same may be true for cortistatin in that expansion of the region may contribute to the basis for a sleep-related or neuronal depressant-related disorder or disease of the brain.

That the mouse iteration sequence is shorter than that of the rat may indicate that the iteration sequence is unstable and subject to expansion as has been seen with other disease states.

2. Oligonucleotides

The invention also contemplates oligonucleotides useful for methods to detect the presence of a cortistatin gene or gene transcript (mRNA) in a tissue by diagnostic detection methods based on the specificity of nucleic acid hybridization or primer extension reactions.

Thus, in one embodiment, any polynucleotide probe having a sequence of a portion of a cortistatin gene of this invention, or a related and specific sequence, is contemplated.

Hybridization probes can be of a variety of lengths from about 10 to 5000 nucleotides long, although they will typically be about 20 to 500 nucleotides in length. Hybridization methods are extremely well known in the art and will not be described further here.

In a related embodiment, detection of cortistatin genes can be conducted by primer extension reactions such as the polymerase chain reaction (PCR). To that end, PCR primers are utilized in pairs, as is well known, based on the nucleotide sequence of the gene to be detected.

Particularly preferred PCR primers can be derived from any portion of a cortistatin DNA sequence, but are preferentially from regions which are not conserved in other cellular proteins.

A preferred PCR primer pair useful for detecting cortistatin genes and cortistatin gene expression are described in the Examples. Nucleotide primers from the corresponding region of cortistatin described herein are readily prepared and used as PCR primers for detection of the presence or expression of the corresponding gene in any of a variety of tissues.

3. Expression Vectors

In addition, the invention contemplates a recombinant DNA molecule (rDNA) containing a DNA segment of this invention encoding a cortistatin protein as described herein. A rDNA can be produced by operatively linking a vector to a DNA segment of the present invention.

As used herein, the term "vector" refers to a DNA molecule capable of autonomous replication in a cell and to which another DNA segment can be operatively linked so as to bring about replication of the attached segment. A vector adapted for expression of a gene product and capable of directing the expression of a cortistatin gene is referred to herein as an "expression vector". Thus, a recombinant DNA molecule is a hybrid DNA molecule comprising at least two nucleotide sequences not normally found together in nature.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector contemplated by the present invention is at least capable of directing the replication, and preferably also expression, of a cortistatin structural gene included in DNA segments to which it is operatively linked.

In one embodiment, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of a cortistatin gene in a bacterial host cell, such as E. coli, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.), pRSET available from Invitrogen (San Diego, Calif.) and pPL and pKK223 available from Pharmacia, Piscataway, N.J.

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), pTDT1 (ATCC, #31255), pRc/CMV (Invitrogen, Inc.), the vector pCMV4 described herein, and the like eucaryotic expression vectors.

In preferred embodiments, the eucaryotic cell expression vectors used to construct the recombinant DNA molecules of the present invention include a selection marker that is effective in an eucaryotic cell, preferably a drug resistance selection marker. A preferred drug resistance marker is the gene whose expression results in neomycin resistance, i.e., the neomycin phosphotransferase (neo) gene. Southern et al., J. Mol. Appl. Genet., 1:327–341 (1982). Alternatively, the selectable marker can be present on a separate plasmid, and the two vectors are introduced by co-transfection of the host cell, and selected by culturing in the appropriate drug for the selectable marker.

4. Inhibitory Nucleic Acids

In accordance with one embodiment of the invention, nucleic acid molecules can be used in methodologies for the inhibition of cortistatin gene expression, thereby inhibiting the function of the cortistatin:cortistatin receptor binding interaction by blocking cortistatin expression.

To that end, the invention contemplates isolated nucleic acid molecules, preferably single-stranded nucleic acid molecules (oligonucleotides), having a sequence complementary to a portion of a structural gene encoding a cortistatin protein of this invention. Nucleic acid-based inhibition is well known and generally referred to as "anti-sense" technology by virtue of the use of nucleotide sequences having complementarity which can hybridize to the "sense" strand or mRNA, and thereby perturb gene expression.

Typical oligonucleotides for this purpose are about 10 to 5,000, preferably about 20–1000, nucleotides in length and have a sequence capable of hybridizing specifically with a structural protein region of the nucleotide sequence that encodes a cortistatin protein of this invention.

In one embodiment, the invention contemplates repetitive units of the nucleotide sequence complementary to a portion of a cortistatin structural gene so as to present multiple sites for complementary binding to the structural gene. This feature may be provided in a single nucleic acid segment having repeating sequences defining multiple portions of a structural gene, by physical conjugation of DNA segments each containing a single portion of a structural gene, or a combination thereof comprising conjugates of DNA segments, each having one or more sequences complementary to a structural gene.

It is also contemplated that nucleotide base modifications can be made to provide certain advantages to a DNA segments of this invention, referred to as nucleotide analogs.

A nucleotide analog refers to moieties which function similarly to nucleotide sequences in a nucleic acid molecule of this invention but which have non-naturally occurring portions. Thus, nucleotide analogs can have altered sugar moieties or inter-sugar linkages. Exemplary are the phosphorothioate and other sulfur-containing species, analogs having altered base units, or other modifications consistent with the spirit of this invention.

Preferred modifications include, but are not limited to, the ethyl or methyl phosphonate modifications disclosed in U.S. Pat. No. 4,469,863 and the phosphorothioate modified deoxyribonucleotides described by LaPlanche et al., Nucl. Acids Res., 14:9081, 1986; and Stec et al., J. Am. Chem. Soc., 106:6077, 1984. These modifications provide resistance to nucleolytic degradation, thereby contributing to the increased half-life in therapeutic modalities. Preferred modifications are the modifications of the 3'-terminus using phosphothioate (PS) sulfurization modification described by Stein et al., Nucl. Acids Res., 16:3209, 1988.

In accordance with the methods of this invention in certain preferred embodiments, at least some of the phosphodiester bonds of the nucleotide sequence can be substituted with a structure which functions to enhance the ability of the compositions to penetrate into the region of cells where the cortistatin structural gene to be inhibited is located. It is preferred that such linkages be sulfur containing as discussed above, such as phosphorotioate bonds. Other substitutions can include alkyl phosphothioate bonds, N-alkyl phosphoramidates, phosphorodithioates, alkyl phosphonates, and short chain alkyl or cycloalkyl structures. In accordance with other preferred embodiments, the phosphodiester bonds are substituted with structures which are, at once, substantially non-ionic and non-chiral.

D. Anti-Cortistatin Antibodies

An antibody of the present invention, i.e., an anti-cortistatin antibody, in one embodiment is characterized as comprising antibody molecules that immunoreact with a cortistatin protein of this invention. Preferably, an antibody further immunoreacts with a cortistatin protein in situ, i.e., in a tissue section.

Thus, the invention describes an anti-cortistatin antibody that immunoreacts with any of the cortistatin polypeptides of this invention, preferably also immunoreacts with the corresponding recombinant cortistatin protein, and more preferably also reacts with a native protein in situ in a tissue section. Preferably, and antibody is substantially free from immunoreaction with a somatostatin protein or neuropeptides other than cortistatin. Assays for immunoreaction useful for assessing immunoreactivity are described herein.

In one embodiment, antibody molecules are described that immunoreact with a cortistatin receptor polypeptide of the present invention and that have the capacity to immunoreact with an exposed site on cortistatin that is required for cortistatin receptor binding. Thus, preferred antibody molecules in this embodiment also inhibit cortistatin receptor function, and are therefore useful therapeutically to block the receptor's function.

Exemplary cortistatin inhibitory antibodies immunoreact with a cortistatin polypeptide described herein that defines an exposed region of a cortistatin protein that is involved in cortistatin receptor function, such as ligand binding.

An antibody of the present invention is typically produced by immunizing a mammal with an inoculum containing a cortistatin polypeptide of this invention and thereby induce in the mammal antibody molecules having immunospecificity for immunizing polypeptide. The antibody molecules are then collected from the mammal and isolated to the extent desired by well known techniques such as, for example, by using DEAE Sephadex to obtain the IgG fraction. Exemplary antibody preparation methods using cortistatin polypeptides in the immunogen are described herein in the Examples.

The term "antibody" in its various grammatical forms is used herein as a collective noun that refers to a population of immunoglobulin molecules and/or immunologically active portions of immunoglobulin molecules, i.e., molecules that contain an antibody combining site or paratope.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules for use in the diagnostic methods and systems of the present invention are intact immunoglobulin molecules, substantially intact immunoglobulin molecules and those portions of an immunoglobulin molecule that contain the paratope, including those portions known in the art as Fab, Fab', F(ab')$_2$ and F(v).

Fab and F(ab')$_2$ portions of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy reduction of the disulfide bonds linking the two heavy chain portions as with mercaptoethanol, and followed by alkylation of the resulting protein mercaptan with a reagent such as iodoacetamide. An antibody containing intact antibody molecules are preferred, and are utilized as illustrative herein.

The preparation of antibodies against polypeptide is well known in the art. See Staudt et al., *J. Exp. Med.*, 157:687–704 (1983), or the teachings of Sutcliffe, J. G., as described in U.S. Pat. No. 4,900,811, the teaching of which are hereby incorporated by reference.

Briefly, to produce a peptide antibody composition of this invention, a laboratory mammal is inoculated with an immunologically effective amount of a cortistatin polypeptide, typically as present in a vaccine of the present invention. The anti-cortistatin antibody molecules thereby induced are then collected from the mammal and those immunospecific for both a cortistatin polypeptide and the corresponding recombinant cortistatin protein are isolated to the extent desired by well known techniques such as, for example, by immunoaffinity chromatography.

To enhance the specificity of the antibody, the antibodies are preferably purified by immunoaffinity chromatography using solid phase-affixed immunizing polypeptide. The antibody is contacted with the solid phase-affixed immunizing polypeptide for a period of time sufficient for the polypeptide to immunoreact with the antibody molecules to form a solid phase-affixed immunocomplex. The bound antibodies are separated from the complex by standard techniques.

The word "inoculum" in its various grammatical forms is used herein to describe a composition containing a cortistatin polypeptide of this invention as an active ingredient used for the preparation of antibodies against a cortistatin polypeptide. When a polypeptide is used in an inoculum to induce antibodies it is to be understood that the polypeptide can be used in various embodiments, e.g., alone or linked to a carrier as a conjugate, or as a polypeptide polymer. However, for ease of expression and in context of a polypeptide inoculum, the various embodiments of the polypeptides of this invention are collectively referred to herein by the term "polypeptide" and its various grammatical forms.

For a polypeptide that contains fewer than about 35 amino acid residues, it is preferable to use the peptide bound to a carrier for the purpose of inducing the production of antibodies.

One or more additional amino acid residues can be added to the amino-or carboxy-termini of the polypeptide to assist in binding the polypeptide to a carrier. Cysteine residues added at the amino-or carboxy-termini of the polypeptide have been found to be particularly useful for forming conjugates via disulfide bonds. However, other methods well known in the art for preparing conjugates can also be used.

The techniques of polypeptide conjugation or coupling through activated functional groups presently known in the art are particularly applicable. See, for example, Aurameas, et al., *Scand. J. Immunol.*, Vol. 8, Suppl. 7:7–23 (1978) and U.S. Pat. Nos. 4,493,795, 3,791,932 and 3,839,153. In addition, a site-directed coupling reaction can be carried out so that any loss of activity due to polypeptide orientation after coupling can be minimized. See, for example, Rodwell et al., *Biotech.*, 3:889–894 (1985), and U.S. Pat. No. 4,671, 958.

Exemplary additional linking procedures include the use of Michael addition reaction products, di-aldehydes such as glutaraldehyde, Klipstein, et al.,*J. Infect. Dis.*, 147:318–326 (1983) and the like, or the use of carbodiimide technology as in the use of a water-soluble carbodiimide to form amide links to the carrier. Alternatively, the heterobifunctional cross-linker SPDP (N-succinimidyl-3-(2-pyridyldithio) proprionate)) can be used to conjugate peptides, in which a carboxy-terminal cysteine has been introduced.

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly D-lysine:D-glutamic acid, and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide per unit dose sufficient to induce an immune response to the immunizing polypeptide depends, among other things, on the species of animal inoculated, the body weight of the animal and the chosen inoculation regimen is well known in the art. Inocula typically contain polypeptide concentrations of about 10 micrograms ($\mu$g) to about 500 milligrams (mg) per inoculation (dose), preferably about 50 micrograms to about 50 milligrams per dose.

The term "unit dose" as it pertains to the inocula refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by, and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent such as water, saline or phosphate-buffered saline to form an aqueous composition.

Inocula can also include an adjuvant as part of the diluent. Adjuvants such as complete Freund's adjuvant (CFA), incomplete Freund's adjuvant (IFA) and at alum are materials well known in the art, and are available commercially from several sources.

The antibody so produced can be used, inter alia, in the diagnostic methods and systems of the present invention to detect cortistatin present in a sample such as a tissue section or body fluid sample. Anti-cortistatin antibodies that inhibit cortistatin function can also be used in vivo in therapeutic methods as described herein.

A preferred anti-cortistatin antibody is a monoclonal antibody.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody.

A preferred monoclonal antibody of this invention comprises antibody molecules that immunoreact with a cortistatin polypeptide of the present invention as described for the anti-cortistatin antibodies of this invention. More preferably, the monoclonal antibody also immunoreacts with recombinantly produced whole cortistatin protein.

A monoclonal antibody is typically composed of antibodies produced by clones of a single cell called a hybridoma that secretes (produces) only one kind of antibody molecule. The hybridoma cell is formed by fusing an antibody-producing cell and a myeloma or other self-perpetuating cell line. The preparation of such antibodies was first described by Kohler and Milstein, Nature 256:495–497 (1975), the description of which is incorporated by reference. The hybridoma supernates so prepared can be screened for the presence of antibody molecules that immunoreact with a cortistatin polypeptide, or for inhibition of cortistatin binding to cortistatin receptor as described herein.

Briefly, to form the hybridoma from which the monoclonal antibody composition is produced, a myeloma or other self-perpetuating cell line is fused with lymphocytes obtained from the spleen of a mammal hyperimmunized with a cortistatin antigen, such as is present in a cortistatin polypeptide of this invention. The polypeptide-induced hybridoma technology is described by Niman et al., Proc. Natl. Acad. Sci. USA, 80:4949–4953 (1983), the description of which is incorporated herein by reference.

It is preferred that the myeloma cell line used to prepare a hybridoma be from the same species as the lymphocytes. Typically, a mouse of the strain 129 GlX$^+$ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md. under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention are identified using the enzyme linked immunosorbent assay (ELISA) described in the Examples.

A monoclonal antibody of the present invention can also be produced by initiating a monoclonal hybridoma culture comprising a nutrient medium containing a hybridoma that produces and secretes antibody molecules of the appropriate polypeptide specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's Minimal Essential Medium (DMEM; Dulbecco et al., Virol. 8:396 (1959)) supplemented with 4.5 gm/l glucose, 20 mM glutamine, and 20% fetal calf serum. An exemplary inbred mouse strain is the Balb/c.

Other methods of producing a monoclonal antibody, a hybridoma cell, or a hybridoma cell culture are also well known. See, for example, the method of isolating monoclonal antibodies from an immunological repertoire as described by Sastry, et al., Proc. Natl. Acad. Sci. USA, 86:5728–5732 (1989); and Huse et al., Science, 246:1275–1281 (1989).

The monoclonal antibodies of this invention can be used in the same manner as disclosed herein for antibodies of the present invention.

For example, the monoclonal antibody can be used in the therapeutic, diagnostic or in vitro methods disclosed herein where immunoreaction with cortistatin is desired.

Also contemplated by this invention is the hybridoma cell, and cultures containing a hybridoma cell that produce a monoclonal antibody of this invention.

E. Diagnostic Methods

The present invention contemplates various assay methods for determining the presence, and preferably amount, of cortistatin in a body sample such as a tissue sample, including tissue mass or tissue section, or in a biological fluid sample using a polypeptide, polyclonal antibody or monoclonal antibody of this invention as an immunochemical reagent to form an immunoreaction product whose amount relates, either directly or indirectly, to the amount of cortistatin in the sample.

Those skilled in the art will understand that there are numerous well known clinical diagnostic chemistry procedures in which an immunochemical reagent of this invention can be used to form an immunoreaction product whose amount relates to the amount of cortistatin in a body sample. Thus, while exemplary assay methods are described herein, the invention is not so limited.

For example, in view of the demonstrated property that cortistatin binds a cortistatin receptor, a cortistatin protein of this invention can be used directly as a probe for detection of a cortistatin receptor by binding thereto.

Additionally, one can use a nucleic acid molecule probes described herein to detect the presence in a cell or tissue of a cortistatin gene or expressed gene in the form of mRNA encoding a cortistatin protein of this invention, as described further herein. Suitable probe-based assays are described by Sutcliffe in U.S. Pat. Nos. 4,900,811 and 5,242,798, the disclosures of which are incorporated by reference.

Various heterogenous and homogeneous protocols, either competitive or noncompetitive, can be employed in performing an assay method of this invention.

For example, one embodiment contemplates a method for assaying the amount of cortistatin protein in a sample that utilizes an anti-cortistatin antibody to immunoreact with cortistatin protein in a sample. In this embodiment, the antibody immunoreacts with cortistatin to form a cortistatin-antibody immunoreaction complex, and the complex is detected indicating the presence of cortistatin in the sample.

An immunoassay method using an anti-cortistatin antibody molecule for assaying the amount of cortistatin in a sample typically comprises the steps of:

(a) Forming an immunoreaction admixture by admixing (contacting) a sample with an anti-cortistatin antibody of the present invention, preferably a monoclonal antibody. The sample is typically in the form of a fixed tissue section in a solid phase such that the immunoreaction admixture has both a liquid phase and a solid phase, and the antibody functions as a detection reagent for the presence of cortistatin in the sample.

Preferably, the sample is a brain tissue sample that has been prepared for immunohistological staining as is well known, although other tissue samples may be adsorbed onto a solid phase, including tissue extracts or body fluid. In that case the adsorption onto a solid phase can be conducted as described for well known Western blot procedures.

(b) The immunoreaction admixture is maintained under biological assay conditions for a predetermined time period such as about 10 minutes to about 16–20 hours at a temperature of about 4° C. to about 45° C. that, such time being sufficient for the cortistatin present in the sample to immunoreact with (immunologically bind) the antibody and form a cortistatin-containing immunoreaction product (immunocomplex).

Biological assay conditions are those that maintain the biological activity of the immunochemical reagents of this invention and the cortistatin sought to be assayed. Those conditions include a temperature range of about 4° C. to about 45° C., a pH value range of about 5 to about 9 and an ionic strength varying from that of distilled water to that of about one molar sodium chloride. Methods for optimizing such conditions are well known in the art.

(c) The presence, and preferably amount, of cortistatin-containing immunoreaction product that formed in step (b) is determined (detected), thereby determining the amount of cortistatin present in the sample.

Determining the presence or amount of the immunoreaction product, either directly or indirectly, can be accomplished by assay techniques well known in the art, and typically depend on the type of indicating means used.

Preferably, the determining of step (c) comprises the steps of:

(I) admixing the cortistatin-containing immunoreaction product with a second antibody to form a second (detecting) immunoreaction admixture, said second antibody molecule having the capacity to immunoreact with the first antibody (primary) in the immunoreaction product.

Antibodies useful as the second antibody include polyclonal or monoclonal antibody preparations raised against the primary antibody.

(ii) maintaining said second immunoreaction admixture for a time period sufficient for said second antibody to complex with the immunoreaction product and form a second immunoreaction product, and (iii) determining the amount of second antibody present in the second immunoreaction product and thereby the amount of immunoreaction product formed in step (c).

In one embodiment, the second antibody is a labeled antibody (i.e., detecting antibody) such that the label provides an indicating means to detect the presence of the second immunoreaction product formed. The label is measured in the second immunoreaction product, thereby indicating the presence, and preferably amount, of second antibody in the solid phase.

Alternatively, the amount of second antibody can be determined by preparation of an additional reaction admixture having an indicating means that specifically reacts with (binds to) the second antibody, as is well known. Exemplary are third immunoreaction admixtures with a labeled anti-immunoglobulin antibody molecule specific for the second antibody. After third immunoreaction, the formed third immunoreaction product is detected through the presence of the label.

Exemplary methods involve the use of in situ immunoreaction methods using tissue sections, or Western blot procedures, as described by Sutcliffe in U.S. Pat. No. 4,900,811.

Another embodiment is contemplated for assaying the amount of therapeutically administered cortistatin protein or anti-cortistatin antibody in a body fluid sample such as cerebrospinal fluid (CSF), blood, plasma or serum. The method utilizes a competition reaction in which either a cortistatin polypeptide or an anti-cortistatin antibody molecule of this invention is present in the solid phase as an immobilized immunochemical reagent, and the other of the two reagents is present in solution in the liquid phase, in the form of a labeled reagent. A fluid sample is admixed thereto to form a competition immunoreaction admixture, and the resulting amount of label in the solid phase is proportional, either directly or indirectly, to the amount of cortistatin polypeptide or antibody in the fluid sample, depending upon the format.

Thus one version of this embodiment comprises the steps of:

(a) Forming a competition immunoreaction admixture by admixing (contacting) a fluid sample with:

(1) an anti-cortistatin antibody according to this invention containing antibody molecules that immunoreact with a cortistatin protein of this invention, said antibody being operatively linked to a solid matrix such that the competition immunoreaction admixture has both a liquid phase and a solid phase, and (2) a polypeptide or recombinant cortistatin protein of the present invention that is immunoreactive with the added antibody. The admixed polypeptide/protein in the liquid phase (labeled competing antigen) is operatively linked to an indicating means as described herein.

(b) The competition immunoreaction admixture is then maintained for a time period sufficient for the competing antigen and the body sample antigen present in the liquid phase to compete for immunoreaction with the solid phase antibody. Such immunoreaction conditions are previously described, and result in the formation of an indicating means-containing immunoreaction product comprising the labeled competing antigen in the solid phase.

(c) The amount of indicating means present in the product formed in step (b) is then determined, thereby determining the presence, and preferably amount, of sample antigen present in the fluid sample.

Determining the indicating means in the solid phase is then conducted by the standard methods described herein.

A reverse version of this embodiment comprises the steps of:

(a) Forming a competition immunoreaction admixture by admixing a fluid sample with:

(1) an anti-cortistatin antibody according to the present invention; and (2) a cortistatin polypeptide or recombinant cortistatin protein of the present invention (capture antigen) that is immunoreactive with the antibody and is operatively linked to a solid matrix such that the competition immunoreaction admixture has both a liquid phase and a solid phase.

(b) The competition immunoreaction admixture is then maintained for a time period sufficient for any cortistatin antigen or anti-cortistatin antibody in the fluid to compete with the admixed antibody molecules for immunoreaction with the solid phase capture antigen and form an antibody-containing immunoreaction product in the solid phase.

(c) The amount of antibody present in the product formed in step (b) is then determined, thereby determining the presence and/or amount of target material in the fluid sample.

In preferred embodiments, the antibody is operatively linked to an indicating means such that the determining in step (c) comprises determining the amount of indicating means present in the product formed in step (b).

Preferably, the fluid sample is provided to a competition immunoreaction admixture as a known amount of CSF, blood, or a blood derived product such as serum or plasma. Further preferred are embodiments wherein the amount of immunochemical reagent in the liquid phase of the immunoreaction admixture is an excess amount relative to the amount of reagent in the solid phase. Typically, a parallel set of competition immunoreactions are established using a known amount of purified recombinant cortistatin or polypeptide in a dilution series so that a standard curve can be developed, as is well known. Thus, the amount of product formed in step (c) when using a fluid sample is compared to the standard curve, thereby determining the amount of target antigen present in the fluid.

In another embodiment, the method for assaying the amount of cortistatin in a sample utilizes a first capture antibody to capture and immobilize cortistatin in the solid phase and a second indicator antibody to indicate the presence of the captured cortistatin antigen. In this embodiment, one antibody immunoreacts with a cortistatin protein to form a cortistatin-antibody immunoreaction complex, and the other antibody is able to immunoreact with the cortistatin while present in the cortistatin-antibody immunoreaction complex. This embodiment can be practiced in two formats with the immobilized capture antibody being either of the two above-identified antibodies, and the indicator antibody being the other of the two antibodies.

Where a antibody is in the solid phase as a capture reagent, a preferred means for determining the amount of solid phase reaction product is by the use of a labeled cortistatin polypeptide, followed by the detection means described herein for other labeled products in the solid phase.

Also contemplated are immunological assays capable of detecting the presence of immunoreaction product formation without the use of a label. Such methods employ a "detection means", which means are themselves well-known in clinical diagnostic chemistry and constitute a part of this invention only insofar as they are utilized with otherwise novel polypeptides, methods and systems. Exemplary detection means include methods known as biosensors and include biosensing methods based on detecting changes in the reflectivity of a surface, changes in the absorption of an evanescent wave by optical fibers or changes in the propagation of surface acoustical waves.

F. Diagnostic Kits

The present invention also describes a diagnostic system, preferably in kit form, for assaying for the presence of a cortistatin of this invention in a body sample, such brain tissue, cell suspensions or tissue sections, or body fluid samples such as CSF, blood, plasma or serum, where it is desirable to detect the presence, and preferably the amount, of a cortistatin protein in the sample according to the diagnostic methods described herein.

In a related embodiment, a nucleic acid molecule can be used as a probe (an oligonucleotide) to detect the presence of a gene or mRNA in a cell that is diagnostic for the presence or expression of a cortistatin in the cell. The nucleic acid molecule probes were described in detail earlier.

The diagnostic system includes, in an amount sufficient to perform at least one assay, a subject cortistatin polypeptide, a subject antibody or monoclonal antibody, and/or a subject nucleic acid molecule probe of the present invention, as a separately packaged reagent.

In another embodiment, a diagnostic system, preferably in kit form, is contemplated for assaying for the presence of a cortistatin polypeptide or anti-cortistatin antibody in a body fluid sample such as for monitoring the fate of therapeutically administered cortistatin polypeptide or anti-cortistatin antibody. The system includes, in an amount sufficient for at least one assay, a subject cortistatin polypeptide and/or a subject antibody as a separately packaged immunochemical reagent.

Instructions for use of the packaged reagent(s) are also typically included.

As used herein, the term "package" refers to a solid matrix or material such as glass, plastic (e.g., polyethylene, polypropylene or polycarbonate), paper, foil and the like capable of holding within fixed limits a polypeptide, polyclonal antibody or monoclonal antibody of the present invention. Thus, for example, a package can be a glass vial used to contain milligram quantities of a contemplated polypeptide or antibody or it can be a microtiter plate well to which microgram quantities of a contemplated polypeptide or antibody have been operatively affixed, i.e., linked so as to be capable of being immunologically bound by an antibody or antigen, respectively.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

A diagnostic system of the present invention preferably also includes a label or indicating means capable of signaling the formation of an immunocomplex containing a polypeptide or antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189–231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-amino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}$I, $^{125}$I, $^{128}$I, $^{132}$I and $^{51}$Cr represent one class of gamma ray emission-producing radioactive element indicating groups. Particularly preferred is $^{125}$I. Another group of useful labeling means are those elements such as $^{11}$C, $^{18}$F, $^{15}$O and $^{13}$N which themselves emit positrons. The positrons so emitted produce gamma rays upon encounters with electrons present in the animal's body. Also useful is a beta emitter, such $^{111}$indium or $^{3}$H.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas, et al., *Scand. J. Immunol.*, Vol. 8 Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the quantity of cortistatin in a sample. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090; No. 3,850,752; and No. 4,016,043, which are all incorporated herein by reference.

Thus, in some embodiments, a cortistatin polypeptide, an antibody or a monoclonal antibody of the present invention can be affixed to a solid matrix to form a solid support that comprises a package in the subject diagnostic systems.

A reagent is typically affixed to a solid matrix by adsorption from an aqueous medium although other modes of affixation applicable to proteins and polypeptides can be used that are well known to those skilled in the art. Exemplary adsorption methods are described herein.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene beads about 1 micron ($\mu$) to about 5 millimeters (mm) in diameter available from Abbott Laboratories of North Chicago, Ill; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems.

G. Cell Lines Expressing Cortistatin

The invention also contemplates a host cell transformed with a recombinant DNA (rDNA) molecule of the present invention. The host cell can be either procaryotic or eucaryotic, although eucaryotic cells are preferred, particularly mammalian cells. Preferred cells are isolated, that is, substantially homogeneous and therefor free from other cell types or other cells having a cortistatin protein expressed therein.

A cell expressing a cortistatin of this invention has a variety of uses according to this invention. Particularly preferred are uses for bulk production of cortistatin, for the purpose of providing immunogen for production of antibody, for supply of therapeutic protein, for direct binding or for screening pharmaceutical compound banks for the presence of cortistatin receptor-specific ligands, i.e., in drug screening assays as described herein. Thus, particularly preferred are cells containing a rDNA molecule that expresses a cortistatin protein of this invention.

In one embodiment, a cell is produced for transplantation into a body tissue, thereby expressing cortistatin and providing replacement therapy. The cell can be syngeneic, and typically will be a brain tissue-derived cell, such as a hippocampal cell, neonatal brain tissue cell, glioma and the like neuronal tissue cell. Transplantation is accomplished using surgical procedures available to a neurosurgeon where the transplantation is to be made into the brain, brain stem or other neurological tissues. In preferred embodiments, the cell contains a vector for expressing the cortistatin in which the expression means is under the control of a regulatable promoter, as is well known, such that expression of cortistatin can be regulated.

Eucaryotic cells useful for expression of a cortistatin protein are not limited, so long as the cell or cell line is compatible with cell culture methods and compatible with the propagation of the expression vector and expression of the cortistatin protein gene product. Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61, NIH Swiss mouse embryo cells NIH/3T3 (ATCC CRL 1658),HELA cells (ATCC CCL 2), baby hamster kidney cells (BHK), COS-7, COS-1, HEK293 (ATCC CRL 1573), Ltk-1, AV-12 (ATCC CRL 9595), and the like eucaryotic tissue culture cell lines.

Transformation of appropriate cell hosts with a recombinant DNA molecule of the present invention is accomplished by well known methods that typically depend on the type of vector used. With regard to transformation of procaryotic host cells, see, for example, Cohen et al., *Proc. Natl. Acad. Sci. USA,* 69:2110 (1972); and Maniatis et al., *Molecular Cloning, A Laboratory Mammal,* Cold Spring Harbor Laboratory, Cold Spring Harbor, N.Y. (1982).

With regard to transformation of vertebrate cells with vectors containing rDNAs, see, for example, Graham et al., *Virol.,* 52:456 (1973); Wigler et al., *Proc. Natl. Acad. Sci. USA,* 76:1373–76 (1979), and the teachings herein.

Successfully transformed cells, i.e., cells that contain a rDNA molecule of the present invention, can be identified by well known techniques. For example, cells resulting from the introduction of an rDNA of the present invention can be cloned to clonally homogeneous cell populations that contain the rDNA. Cells from those colonies can be harvested, lysed and their DNA content examined for the presence of the rDNA using a method such as that described by Southern, *J. Mol. Biol.,* 98:503 (1975) or Berent et al., *Biotech.,* 3:208 (1985).

In addition to directly assaying for the presence of rDNA, successful transformation can be confirmed by well known immunological methods when the rDNA is capable of directing the expression of cortistatin or by the detection of cortistatin binding activity.

For example, cells successfully transformed with an expression vector produce proteins displaying cortistatin antigenicity or biological activity. Samples of cells suspected of being transformed are harvested and assayed for either cortistatin biological activity or antigenicity.

Thus, in addition to the transformed host cells themselves, the present invention also contemplates a culture of those cells, preferably a monoclonal (clonally homogeneous) culture, or a culture derived from a monoclonal culture, in a nutrient medium. Preferably, the culture also contains a protein displaying cortistatin antigenicity or biologically activity.

Nutrient media useful for culturing transformed host cells are well known in the art and can be obtained from several commercial sources. In embodiments wherein the host cell is mammalian, a "serum-free" medium can be used.

H. Screening Methods to Identify Agonists and Antagonists of Cortistatin

The ability to selectively bind/modulate function of a cortistatin receptor by a cortistatin ligand is at the heart of useful cortistatin pharmacology, and depends on identifying pharmacological molecules which can act a selective ligands, agonists or antagonists for a cortistatin receptor. To that end, the elucidation of new cortistatin proteins, such as those described herein, provides valuable tools for the search for selective reagents, tools that are useful in binding assays, and in screening assays which indicate selective drug response to the cortistatin receptor.

Thus, the invention contemplates methods for determining whether a molecule binds to, and preferably whether the molecule activates, a preselected cortistatin receptor.

The method comprises conducting a binding assay to identify molecules which bind the cortistatin receptor, as described in any of the assays herein. Thus, the method comprises (1) contacting a candidate molecule with a cell having a cortistatin receptor under conditions permitting binding of cortistatin to the receptor, and (2) detecting the presence of the candidate molecule bound to the cortistatin receptor, thereby determining whether the candidate binds to the receptor. The receptor is typically a cell surface protein when expressed by the cells.

Alternatively, one can use a competition format to identify analogs of cortistatin by using a labeled cortistatin, and measuring the amount of bound label in the presence of a candidate ligand, indicating whether the candidate competes with labeled cortistatin for binding to the receptor. An exemplary competition assay is described herein.

It is also possible to use the above method to determine whether the molecule which binds to the cortistatin receptor also activates or motivates the receptor's function, i.e., acts as an agonist, or determine whether the molecule inhibits the receptor's function, i.e., acts as an antagonist. Thus, by evaluating in the detecting step whether the cortistatin receptor is activated, one determines whether the candidate molecule is bioactive.

Methods for detecting bioactivity of the candidate molecule can vary, but typically involve measuring changes in intracellular levels of a secondary messenger effected as a result of binding, detecting changes in electrical potential, observing physiological or behavioral effects related to cortistatin function, and the like methods. Exemplary assays for binding or for cortistatin-specific bioactivity are described in the Examples and include measurement of hyperpolarization of hippocampal cells, measurement of induction of slow wave sleep waveform two (SWS2), direct binding to a cell having a cortistatin receptor, assaying accumulation of cAMP, and the like assays.

It is noted that the cortistatin receptor has not been characterized in extensive detail. It is known that cortistatin binds to the somatostatin receptor, for which there are several species of receptor, and it is known that cortistatin also binds a more specific receptor, designated for convenience as the "true" cortistatin receptor, although the binding reaction with the somatostatin receptor is likely a real physiological event, making it a "true" receptor for some purposes. Thus, any receptor that binds cortistatin can be referred to as a cortistatin receptor for the purposes of a screening assay, although receptors with the highest affinity and specificity for cortistatin are preferred. In practicing the present screening methods, one can use any of a variety of cells lines or tissues that possess a cortistatin receptor, including the exemplary cell lines and tissues described herein. The invention should not be construed as limiting so long as the binding or bioactivity assay involves the use of a cortistatin receptor. In preferred embodiments, a receptor that is specific for cortistatin should be used. Specificity can be demonstrated by well known methods of ligand binding and ligand-mediated activation.

Thus, a related embodiment contemplates a method for screening to identify a candidate molecule that can bind, inhibit or activate a preselected cortistatin receptor by functioning as a cortistatin agonist or antagonist. The method comprises:

(a) contacting a mammalian cell with said candidate drug under conditions permitting activation of said cortistatin receptor by cortistatin; and (b) detecting the activation status of said cortistatin receptor, and thereby determining whether the drug activates or inhibits said receptor.

I. Methods for Altering Cortistatin Receptor Function

1. Therapeutic Methods

It is contemplated that the certain reagents described in the present invention have the capacity to modulate cortistatin receptor function, such as agonists or antagonists, and therefore are useful in therapeutic methods for conditions mediated by the cortistatin receptor.

Cortistatin polypeptides that mimic exposed regions of cortistatin have the ability to function as analogs and compete for binding to the cortistatin receptor, or for other agents that would normally interact with the receptor, thereby inhibiting binding of cortistatin to the receptor.

Furthermore, antibodies and monoclonal antibodies of the present invention that bind to exposed regions of cortistatin have the capacity to alter cortistatin receptor function by blocking natural interactions with cortistatin that normally interact at the site. Exemplary antibodies are the anti-cortistatin antibodies described earlier.

Finally, oligonucleotides are described herein which are complementary to mRNA that encodes a cortistatin protein of this invention and that are useful for reducing gene expression and translation of the cortistatin mRNA, thereby altering cortistatin levels in a tissue.

Thus, in one embodiment, the present invention provides a method for modulating cortistatin function in a animal or human patient comprising administering to the patient a therapeutically effective amount of a physiologically tolerable composition containing a cortistatin polypeptide, analog or peptidomimetic, anti-cortistatin antibody or monoclonal antibody, cortistatin agonist or antagonist, or an oligonucleotide of the present invention.

A therapeutically effective amount of a cortistatin polypeptide, as an example for practicing the invention, is a predetermined amount calculated to achieve the desired effect, i.e., to inhibit receptor interaction with its normal target, and thereby interfere with normal receptor function.

Similarly, a therapeutically effective amount of an anti-cortistatin antibody is a predetermined amount calculated to achieve the desired effect, i.e., to immunoreact with the cortistatin, and thereby inhibit the cortistatin receptor's ability to interact with its normal target, cortistatin, and thereby interfere with normal receptor function.

The in vivo inhibition of cortistatin receptor function using a cortistatin polypeptide, an anti-cortistatin antibody, or cortistatin agonist or antagonist of this invention is a particularly preferred embodiment and is desirable in a variety of clinical settings, such as where the patient is exhibiting symptoms of an over or under activated cortistatin receptor.

A therapeutically effective amount of a cortistatin polypeptide, agonist or antagonist of this invention is typically an amount such that when administered in a physiologically tolerable composition is sufficient to achieve a plasma concentration of from about 0.1 micromolar ($\mu$M) to about 100 $\mu$M, and preferably from about 0.5 $\mu$M to about 10 $\mu$M.

A therapeutically effective amount of an antibody of this invention is typically an amount of antibody such that when administered in a physiologically tolerable composition is sufficient to achieve a plasma concentration of from about 0.1 microgram ($\mu$g) per milliliter (ml) to about 100 $\mu$g/ml, preferably from about 1 $\mu$g/ml to about 5 $\mu$g/ml, and usually about 5 $\mu$g/ml.

The effectiveness of the therapy can be determined by observing ablation of the symptoms associated with the function of the cortistatin receptor being inhibited.

The therapeutic compositions containing a cortistatin polypeptide, agonist, antagonist or anti-cortistatin antibody of this invention are conventionally administered intravenously or by a method for delivery to a brain tissue, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

Delivery to a brain tissue or CSF can be accomplished by a variety of means, including by direct injection, by use of a cannula into the target tissue, by direct application in a surgical procedure, by adsorption across the blood-brain barrier following intravenous administration, and the like means.

The therapeutic compounds and compositions are generally administered so as to contact the cells or the tissue containing cells which contain the target cortistatin receptor. This administration can be accomplished by introduction of the composition internally such as orally, intravenously, intramuscularly, intranasally or via inhalation of aerosols containing the composition, and the like, by cannula into a brain tissue, or by introduction into or onto a tissue system as by introduction transdermally, topically or intralesionally, in suppositories, or by intra-orbital injection, and the like.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are particular to each individual. However, suitable dosage ranges for systemic application are disclosed herein and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the CSF or blood in the ranges specified for in vivo therapies are contemplated.

As an aid to the administration of effective therapeutic amounts of a cortistatin polypeptide, agonist, antagonist, antibody, or monoclonal antibody, (hereinafter a "therapeutic agent") a diagnostic method of this invention for detecting a therapeutic agent in the subject's CSF or blood is useful to characterize the fate of the administered therapeutic agent. Suitable diagnostic (monitoring) assays are described herein.

2. Methods for Inhibiting Gene Expression

In another embodiment, the invention contemplates the use of nucleic acids encoding portions of a cortistatin gene for inhibiting gene expression and function.

Thus, the present invention provides for a method for inhibiting expression of cortistatin gene products and thereby inhibiting the function of the target cortistatin protein. The DNA segments and their compositions have a number of uses, and may be used in vitro or in vivo. In vitro, the compositions may be used to block function and/or expression of cortistatin in cell cultures, tissues, organs and the like materials that can express cortistatin. In vivo, the compositions may be used prophylactically or therapeutically for inhibiting expression of a cortistatin gene, and by inhibiting diseases or medical conditions associated with the expression or function of the cortistatin gene or the activity state of its receptor.

The method comprises, in one embodiment, contacting cells or tissues with a therapeutically effective amount of a pharmaceutically acceptable composition comprising a DNA segment of this invention. In a related embodiment, the contacting involves introducing the DNA segment composition into cells expressing a cortistatin protein.

The DNA segment can be in a variety of forms, but is preferably in a single-stranded form to facilitate complementary hybridization to the target mRNA in the cell in which the cortistatin gene expression is to be altered.

The term "cells" is intended to include a plurality of cells as well as single cells. The cells can be isolated, or can be cells that form a larger organization of cells to form a tissue or organ.

In a further embodiment, the invention contemplated the method of inhibiting the expression of cortistatin genes in a patient comprising administration to the patient of a therapeutically effective amount of a DNA segment composition of this invention in a pharmaceutically acceptable excipient. In cases where the distribution of the cortistatin is believed to be disseminated in the body, the administration of therapeutic oligonucleotide can be systemic. Alternatively, the target cortistatin can be localized to a tissue, and the therapeutic method can likewise be directed at delivering the therapeutic DNA segment to the tissue to be treated.

The concentration of the active DNA segment ingredient in a therapeutic composition will vary, depending upon the desired dosage, use, frequency of administration, and the like. The amount used will be a therapeutically effective amount and will depend upon a number of factors, including the route of administration, the formulation of the composition, the number and frequency of treatments and the activity of the formulation employed.

The use of therapeutic DNA segments, and therefore the delivery of those DNA segments into cells where they are effective, has been described in a variety of settings. It is generally known that therapeutically effective intracellular levels of nucleic acids, and particularly smaller nucleic acids such as DNA segments and oligonucleotides, can be achieved by either exposing cells to solutions containing nucleic acids or by introduction of the nucleic acids into the inside of the cell. Upon exposure, nucleic acids are taken up by the cell where they exert their effectiveness. In addition, direct introduction into the cell can be provided by a variety of means, including microinjection, delivery by the use of specific uptake vehicles, and the like.

The pharmaceutical composition containing the therapeutic oligonucleotide preferably also contains physiologically acceptable carriers, in particular hydrophobic carriers which facilitate carrying the oligonucleotide through the cell membrane or blood brain barrier.

Exemplary descriptions of the delivery of therapeutic DNA segments and oligonucleotides into cells can be found in the teachings of U.S. Pat. Nos. 5,04,820, 4,806,463, 4,757,055, and 4,689,320, which teachings are hereby incorporated by reference.

A therapeutically effective amount is a predetermined amount calculated to achieve the desired effect, i.e., to bind to a cortistatin gene present and thereby inhibit function of the gene.

As is apparent to one skilled in the art, the copy number of a cortistatin gene may vary, thereby presenting a variable amount of target with which to hybridize. Thus it is preferred that the therapeutic method achieve an intracellular concentration of a therapeutic DNA segment of this invention in molar excess to the copy number of the gene in the cell, and preferably at least a ten-fold, more preferably at least a one-hundred fold, and still more preferably at least a one thousand-fold excess of therapeutic DNA segments relative to the gene copy number per cell. A preferred effective amount is an intracellular concentration of from about 1 nanomolar (nM) to about 100 micromolar ($\mu$M), particularly about 50 nM to about 1 $\mu$M.

Alternatively, a therapeutically effective amount can be expressed as an extracellular concentration. Thus it is preferred to expose an cell containing a cortistatin gene to a concentration of from about 100 nM to about 10 millimolar (mM), and preferably about 10 $\mu$M to 1 mM. Thus, in embodiments where delivery of a therapeutic DNA segment composition is designed to expose cells to the nucleic acid for cellular uptake, it is preferred that the local concentration of the DNA segment in the area of the tissue to be treated reach the extracellular concentrations recited above.

For patient dosages, using a 20 nucleotide base double-stranded DNA segment as the standard, a typical dosage of therapeutic composition for a 70 kilogram (kg) human contains in the range of about 0.1 milligram (mg) to about 1 gram of 20-mer DNA segment per day, and more usually in the range of about 1 mg to 100 mg per day. Stated differently, a dosage of about 1 $\mu$g/kg/day to about 15 mg/kg/day, and preferably about 15 to 1500 $\mu$g/kg/day is contemplated.

The in vivo inhibition of cortistatin gene expression and/or function by a therapeutic composition of this invention is desirable in a variety of clinical settings, such as where the patient is at risk for disease based on expression of the cortistatin gene.

3. Therapeutic Compositions

The present invention contemplates therapeutic compositions useful for practicing the therapeutic methods described herein. Therapeutic compositions of the present invention contain a physiologically tolerable carrier together with a therapeutic reagent of this invention, namely a cortistatin polypeptide, an anti-cortistatin antibody or monoclonal antibody, or oligonucleotide as described herein, dissolved or dispersed therein as an active ingredient. In a preferred embodiment, the therapeutic composition is not immunogenic when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

As described herein, for intracellular delivery of oligonucleotides, specialized carriers may be used which facilitate transport of the oligonucleotide across the cell membrane. These typically are hydrophobic compositions, or include additional reagents which target delivery to and/or into cells.

Liquid compositions can also contain liquid phases in addition to and to the exclusion of water. Exemplary of such additional liquid phases are glycerin, vegetable oils such as cottonseed oil, and water-oil emulsions.

A therapeutic composition contains an amount of a cortistatin polypeptide or anti-cortistatin antibody molecule of the present invention sufficient to inhibit cortistatin function. Typically this is an amount of at least 0.1 weight percent, and more preferably is at least 1 weight percent, of peptide or antibody per weight of total therapeutic composition. A weight percent is a ratio by weight of peptide or antibody to total composition. Thus, for example, 0.1 weight percent is 0.1 grams of polypeptide per 100 grams of total composition.

EXAMPLES

The following examples are intended to illustrate but are not to be construed as limiting the specification and claims in any way.

1. Identification of Cortistatin Nucleic Acids

A. Rat cDNA

To screen for novel mRNAs, an 140 base pair (bp) cDNA clone was obtained from a subtracted rat hippocampal library and then used as a probe to screen a rat brain cDNA library in the plasmid pHG327 as described by Forss-Petter et al., *J. Mol. Neurosci.*, 1:63–75 (1989). The cDNA library was constructed as described by Staeheli et al., *Cell*, 44:147–158 (1986), the disclosure of which is hereby incorporated by reference.

Briefly, the subtracted cDNA library was constructed essentially as described by Usui et al., *J. Neurosci.*, 14:4915–4926 (1994) and was the result from subtracting a cDNA library made from hippocampi of rats that had been stimulated at high frequency in vivo (referred to as the target library in Usui et al.) with a cDNA library made from the contralateral hippocampi of the same rats (referred to as the driver cDNA library). Clones from this subtracted library were arrayed on nylon replica filters and hybridized with probes consisting of the target and driver cDNA libraries. cDNA clones hybridizing with the target but not the driver were further analyzed by dideoxy sequencing (Sanger et al.*Proc. Natl. Acad. Sci. USA*, 74:5463–5467 (1977) and in situ hybridization (de Lecea et al., *Mol. Brain Res.*, 25:286–296 (1994). The 140 base pair (bp) long nucleotide sequence of clone 1D4 (later named preprocortistatin), that was used as the above-described screening probe, was then compared with sequences in the GenBank database and was recognized by having a significant degree (82%) of similarity with the nucleotide sequence reported for somatostatin.

Further screens of whole rat brain and hippocampal cDNA libraries produced five additional clones up to 438 nucleotides in length, including two displaying an initiator methionine codon. The nucleotide sequence of the isolated clones was determined using the dideoxy method as described by Sanger et al., *Proc. Natl. Acad. Sci., USA*, 74:5463–5467 (1977). Sequence alignment was performed with the BESTFIT program (GCG group, University of Wisconsin).

From the five cDNA clones obtained from screening the above-identified libraries, a complete coding nucleotide sequence of rat preprocortistatin cDNA, 438 nucleotides in length, was compiled as shown in FIG. 1 and listed in SEQ ID NO 1. The complete preprocortistatin cDNA clone displays a 336 nucleotide open reading frame (ORF) with a N-terminal signal peptide whose cleavage site is indicated by an arrow between amino acid positions 27 and 28 corresponding to a cleavage site after nucleotide position 110. A sequence of six iterations of the trinucleotide CTG repeats encoding leucine residues contained within the coding region for the signal peptide is underlined. Such a triplet expansion in other genes has been implicated as causal in neurological diseases, e.g., myotonic dystrophy as described by Brook et al., *Cell*, 68:799–808 (1992).

Translation of this rat cDNA sequence indicated that a novel protein of 112 amino acid residues, called rat preprocortistatin, was encoded as shown in FIG. 1 aligned under the cDNA sequence. The deduced amino acid sequence of rat preprocortistatin is also listed in SEQ ID NO 1 with the nucleotide sequence and in SEQ ID NO 2 alone.

Cleavage of the preprospecies to procortistatin would produces a mature protein that is processed at either of two tandem basic amino acid pairs, KK (lys-lys) or KR (lys-arg) shown in bold in FIG. 1, to produce cortistatin-29 and cortistatin-14, the latter shown in FIG. 1 in the solid lined box, analogous to the cleavage of preprosomatostatin at 28 and 14 residues as described by Glushankov et al., *Proc. Natl. Acad. Sci., USA*, 81:6662–6666 (1984), or at both basic pairs to additionally produce cortistatin-13, shown in FIG. 1 with the hatched lined box. Whereas cortistatin-13 is unrelated to known species, cortistatin-14 shares 11 of 14 residues with somatostatin-14. Alignment of rat preprocortistatin with the 116 amino acid residue sequence of preprosomatostatin is shown in FIG. 2 labeled respectively as CST and SST. Single dots between the sequences indicate non-conservative amino acid substitutions while double vertical dots indicate conservative amino acid substitutions. Vertical lines between the sequences indicate identity between CST and SST. Single dots between the continuous sequence of CST indicate spacing to accommodate for the alignment with SST. The amino acid residue sequence of CST shown in FIG. 2 corresponds to positions 10 to 112 in SEQ ID NO 2. The amino acid residue sequence of SST is listed in SEQ ID NO 3.

The shared amino acids between preprocortistatin and preprosomatostatin include two cysteine residues that are likely to render the peptide cyclic and the FWKT amino acid residues (SEQ ID NO 2 from position 104 to 107) that are critical for somatostatin binding to its receptors as described by Veber et al., *Nature* 280:512–514 (1979). However, extended amino acid identity is seen only at their C-termini. Both statins share the critical residues for binding to the receptors as shown in bold in the figure and the cysteines that are likely to render the peptides cyclic.

As shown in FIG. 2, for the portion of the preprostatin sequences beginning after the bold KK for CST and the bold RK for SST indicating peptides with 14 amino acids, the cortistatin-14 and somatostatin-14 are permuted by one amino acid. Thus, the alignment of cortistatin begins at the second amino acid of the somatostatin-14 peptide, corresponding to amino acid residue position 104 in FIG. 2, and cortistatin terminates with a lysine residue that extends one amino acid residue, corresponding to CST amino acid position 112, beyond the C-terminal cysteine of somatostatin. This difference and their cDNA sequences indicate clearly that they are the products of separate genes.

B. Mouse cDNA

A mouse (C57/B16) cerebral cortex cDNA library, constructed in the pT7T3D vector (Pharmacia, Piscataway, N.J.) was similarly screened to obtain the mouse homolog to the rat preprocortistatin cDNA obtained above. The screens produced four additional clones up to 430 nucleotides in length, including two displaying a initiator methionine codon. The nucleotide sequence of the isolated clones was determined as described above as was alignment of the sequences.

From the four cDNA clones obtained from screening the above-identified libraries, a complete coding nucleotide sequence of mouse preprocortistatin cDNA, 427 nucleotides in length, was compiled as shown in FIG. 3 and listed in SEQ ID NO 4. The complete preprocortistatin cDNA clone displays a 327 nucleotide open reading frame (ORF) with a N-terminal signal peptide whose cleavage site is indicated by an arrow between amino acid positions 25 and 26 corresponding to a cleavage site after nucleotide position 99. A sequence of three iterations of the trinucleotide CTG encoding leucine residues contained within the coding region for the signal peptide is underlined.

Translation of this mouse cDNA sequence indicated that a novel protein of 109 amino acid residues, called mouse preprocortistatin, was encoded as shown in FIG. 3 aligned under the cDNA sequence. The deduced amino acid sequence of mouse preprocortistatin is also listed in SEQ ID NO 4 with the nucleotide sequence and in SEQ ID NO 5 alone.

Similar to the rat preprocortistatin, cleavage of the mouse preprospecies to procortistatin produces a mature protein that is processed at either of two tandem basic amino acid pairs, KS (lys-ser) and KK (lys-lys) shown in bold in FIG. 3, to produce mouse cortistatin-29 and mouse cortistatin-14, the latter shown in FIG. 3 in the solid lined box, or at both basic pairs to additionally produce mouse cortistatin-13, shown in FIG. 3 with the hatched lined box.

After introduction of two gaps, the mouse and rat nucleotide sequences were 86% identical. Assuming that the mouse translation initiation product begins at the second methionine triplet, it contains 108 amino acids compared to 112 for rat. Again, after introduction of two gaps, the encoded rat and mouse proteins share 82% identity. The mouse nucleotide sequence corresponding to cortistatin-14 and the adjacent lysine doublet that serves as its site of proteolytic release from its precursor were identical to same region in the rat sequence, thus supporting a functional conservation of the mature peptide. The DNA sequence upstream from the processing site of cortistatin-14 showed several points of divergence, including some resulting in non-conservative amino acid substitutions. The sequence corresponding to the signal peptide of preprocortistatin contains only three iterations of CTG encoding the amino acid leucine, in contrast to six iterations of the same triplet in the rat peptide precursor, indicating that this sequence is unstable and subject to expansion.

C. Human cDNA

The human homolog is similarly obtained from screening human brain cDNA libraries essentially as described above for rat and mouse cortistatin nucleic acids and proteins. To screen for novel mRNAs, a 120 bp fragment of the human coding sequence was isolated by PCR using degenerate primers from the mouse and rat sequences. The nucleotide sequence of this fragment was compared to the EST database and one sequence was found with significant similarity to cortistatin. A 250 bp nucleotide fragment was obtained and used as a probe to screen a human whole brain cDNA library. The screens produced two cDNA clones, 450 and 270 nucleotides in length, and the sequence from the longest was determined. Human preprocortistatin cDNA was amplified by PCR using primers to the C-terminal sequence of cortistatin. The PCR fragment was cloned, random prime labeled and used to screen a cDNA library prepared from human whole brain mRNA (Clontech).

A complete coding nucleotide sequence of human preprocortistatin cDNA, 701 nucleotides in length, was compiled as shown in FIG. 3a and listed in SEQ ID NO 25. A sequence of four iterations of the trinucleotide CTG encoding leucine residues contained within the coding region for the signal peptide is underlined in FIG. 3a. The complete preprocortistatin cDNA clone displays a 315 ORF, which begins at position 78 of SEQ ID NO 25.

Translation of this human cDNA sequence indicated that a novel protein of 105 amino acid residues, called human preprocortistatin, was encoded as shown in FIG. 3b. The deduced amino acid sequence of human preprocortistatin is listed in SEQ ID NO 26.

Similar to the rat preprocortistatin, cleavage of the human preprospecies to procortistatin generates a mature protein that is processed at either of two RR (arg-arg) tandem basic amino acid pairs, to produce human cortistatin-29 and human cortistatin-17. The human preprospecies along with the prospecies and the mature proteins are listed in Table 1 in the Examples including their noted amino acid residue sequences.

The human and rat nucleotide sequences are 71% identical. The human cortistatin-17 shares 13 of the last 14 residues with rat and mouse cortistatin-14. The lysine doublet that lies just N-terminal to cortistatin-14 in the rat and mouse is not conserved in the human sequence. The DNA sequence upstream from the processing site of cortistatin-14 are not very conserved across species. However, rat cortistatin-31 and human cortistatin-31 share 13 residues clustered in their N-terminal regions that are conserved among the rat, mouse, and human prohormone sequences. The sequence corresponding to the signal peptide of preprocortistatin contains only four iterations of CTG encoding the amino acid leucine, in contrast to six iterations of the same triplet in the rat peptide precursor or three in mouse, indicating that this sequence is unstable and subject to expansion.

2. Preparation of Cortistatin Protein and Polypeptides

A. Recombinant Proteins

Rat preprocortistatin (SEQ ID NO 1) is inserted into the BamH1 sites of the pHG237 vector, both the DNA and vector are described above. Upon digestion with BamH1 restriction enzyme, the resultant 450 bp fragment is then inserted directly into the BglII site of the polylinker region of the pCM4 vector (David W. Russell, Dept. of Molecular Genetics, University of Texas Southwestern Medical Center, Dallas, Tex.). This vector uses the cytomegalovirus (CMV) promoter to direct the expression of foreign proteins in mammalian cells. Several eight to ten amino acid epitope "tags" are added by PCR to the N-terminal of preprocortistatin to allow visualization of the processed product in mammalian cells.

For example, the respective 5' and 3' synthetic oligonucleotides, written in the 5' to 3' direction, 5' ATC-GAGATCTAAGGAGGATGGGTGGCTGCAG3' (SEQ ID NO 13) and 5' ACTGTCTAGATCATAGGTCTTCTTCT-GATATTAGTTTTTGTTCCTTGCACGA GGAGAAG-GTTTTCCAG3' (SEQ ID NO 14) are used as primers in PCR to amplify preprocortistatin beginning at nucleotide position 23 in SEQ ID NO 1 with an inserted BglII site added at its 5' end to the 3' end having an inserted c-myc epitope tag. The 5' primer is also referred to as an upstream, sense or forward primer. The 3' primer is also referred to as a downstream, anti-sense or backward primer. The resultant PCR products are such that, when subcloned into the pCMV or related vectors and transfected into mammalian cells (CHO, AtT-20 or GH4 cells), produce a procortistatin-myc tagged protein product that is visualized by Western blot or immunocytochemistry, without the need of cortistatin-specific antibodies. For in vivo visualization of the processing, the preprocortistatin sequence amplified as described above could be inserted into the pGFP-N1 vector (Clontech, Palo Alto, Calif.), which contains the green fluorescein protein (GFP) from Aecuorea victoria.

Procortistatin proteins for use in this invention are also produced in bacteria and purified by subcloning the procortistatin coding sequence described above and seen in FIG. 1 into the pRSET B vector (Invitrogen, San Diego, Calif.), which contains the nucleotide sequence encoding 6 histidines before the insertion of the procortistatin sequence. The vector contains the T7 promoter which drives the expression of 6×His-tagged proteins in E. coli. For this aspect, the respective synthetic 5' and 3' oligonucleotides, 5' ATCGAGATCTGTCCTGGAGA3' (SEQ ID NO 15) and 5' ACTGAATTCAGGCCACGGCTGCATTCACAG 3' (SEQ ID NO 16), are used as primers in PCR to amplify the rat preprocortistatin sequence without the signal peptide into the BglII and EcoRI sites of the pRSET B vector. Once expressed, the expressed 6×histidine-tagged procortistatin sequence is then purified by affinity chromatography on a TALON (Clontech) metal affinity resin.

A procortistatin-glutathione-S-transferase fusion protein (CST-GST) is produced in E. coli by subcloning the procortistatin sequence into the appropriate sites of the pGEX2 vector (Pharmacia), as described above.

Thus, the methods described herein are useful for the generation of both recombinant cortistatin proteins and recombinant cortistatin fusion proteins. With the above-described expression methods, mouse and human homologs of the rat procortistatin are similarly prepared along with the remaining rat and mouse cortistatin proteins and peptides listed below in Table 1. The cloning and expression of the cortistatin proteins and polypeptides of this invention are techniques well known to one of ordinary skill in the art and are described, for example, in "Current Protocols in Molecular Biology", eds. Ausebel et al., Wiley & Sons, Inc., New York (1989), the disclosures of which are hereby incorporated by reference.

Once expressed, the recombinant cortistatin proteins and polypeptides along with fusion proteins thereof are useful in the screening methods, diagnostic methods and therapeutic modalities as described below. Specifically, with respect to screening methods, recombinant cortistatins are used in the solid phase in assays including Western blot, ELISA, RIA, and the like, all of which are well known techniques in the art. Similarly, the molecules described herein are used in liquid phase in assays including receptor binding assays for direct binding or for competition of binding (see Example 5), for cAMP activation assays (see Example 5), for identifying cortistatin-specific receptors (see Example 7), and the like. The determination and identification of cortistatin analogs and antagonists is also facilitated with the use of recombinant cortistatin proteins and polypeptides as described in Example 6. Therapeutic uses of recombinant molecules are similarly described in Example 8. Other uses not described herein of the molecules of the present invention are also contemplated.

B. Synthetic Proteins and Polypeptides

An alternative method to preparing recombinant cortistatin proteins and polypeptide is preparing synthetic versions thereof. For this procedure, the polypeptides were synthesized using standard solid-phase synthesis techniques as, for example, described by Merrifield, *Adv. Enzymol.*, 32:221–296 (1969), and Fields, G. B. and Noble, R. L., *Int. J. Peptide Protein Res.*, 35:161–214 (1990) and as described in U.S. Pat. Nos. 4,900,811 and 5,242,798, the disclosures of which are hereby incorporated by reference.

The various cortistatin proteins and peptides of this invention are hereinafter referred to by their designations as listed in Table 1. The corresponding SEQ ID NO for each peptide is also listed in Table 1.

Table 1

TABLE 1

| Designation | SEQ ID NO | Figure |
|---|---|---|
| rat preprocortistatin | 2 | 1-complete sequence |
| rat procortistatin | 6 | 1-from arrow to end |
| rat cortistatin-29 | 7 | 1-from beginning of hatched line to end |
| rat cortistatin-14 | 8 | 1-in solid box |
| rat cortistatin-13 | 9 | 1-in hatched box |
| mouse preprocortistatin | 5 | 3-complete sequence |
| mouse procortistatin | 10 | 1-from arrow to end |
| mouse cortistatin-29 | 11 | 3-from beginning of hatched line to end |
| mouse cortistatin-14 | 8 | 3-in solid box |
| mouse cortistatin-13 | 12 | 3-in hatched box |

TABLE 1-continued

| Designation | SEQ ID NO | Figure |
|---|---|---|
| human preprocortistatin | 26 | 3a-complete sequence |
| human cortistatin-29 | 26 | 3a-from arrow to end |
| human cortistatin-17 | 26 | 3a-in solid box |
| human cortistatin-31 | 26 | 3a-in hatched box |

The cortistatin-14 peptide, having the same amino acid residue sequence forrat and mouse, was synthesized in the carboxy-terminal amide form. It was then analyzed by reverse phase high performance liquid chromatography (HPLC) on a Vydac C-18 column (Alltech Associates, Inc., IL) with a 0–60% acetonitrile linear gradient in 0.1w trifluoroacetic acid. The peptide was then purified to homogeneity by preparative HPCL using optimal conditions suggested by the analytical chromatography. The amino acid composition and concentration of the isolated peptide was determined with a 24 hour hydrolysis in 6 N HCl in evacuated tubes at 110 degrees Celsius (110° C.) and subsequent analysis on a Beckman Model 6300 High Performance Analyzer.

After purification, the peptide was separately resuspended in distilled water to form a dissolved peptide solution at a final concentration of 2.5 mM. Subsequently, one-tenth volume of 10-fold concentrated buffer, referred to as TBS-Az containing 0.05 M Tris hydroxymethyl aminomethane-hydrochloride (Tris-HCl) at pH 7.4 0.1 M sodium chloride (NaCl), 0.02% sodium azide (NaN$_3$), was added. The pH of the solution was checked, and if necessary, adjusted to pH 7.4 with titrated amounts of 1 M Tris-base.

The remaining cortistatin proteins and peptides listed in Table 1 are similarly synthesized and purified for use in practicing this invention.

3. Preparation of Anti-Cortistatin Antibodies

A. Preparation of Polyclonal Antisera to Synthetic Polypeptides

1) Preparation of Immunogen

For preparation of a peptide immunogen, the synthetic polypeptide cortistatin-14 was prepared as described in Example 2. The synthesized peptide was coupled to edestin (Sigma, St. Louis, Mo.) using the heterobifunctional crosslinking agent, N-succinimidyl-3-(2-pyridyldithio) propionate (SPDP) (Pierce Biochemicals, Rockford, Ill.). For the coupling procedure, 80 microliters (1) of 10 milligrams/milliliter (mg/ml) SPDP dissolved in dimethylformamide was admixed dropwise to 400 1 15 mg/ml edestin in 0.1 M phosphate, 0.1 M NaCl at pH 8.5 under continuous stirring conditions for 30 minutes at 22° C. in order to form SPDP-activated edestin.

The resultant SPDP-activated edestin was then extensively dialyzed at 4° C. against a buffered solution of 0.1 M phosphate and 0.1 M NaCl at pH 7.4 in order to remove uncoupled SPDP. Six mg of prepared peptide was first dissolved in 2 ml of 0.1 M phosphate and 0.1 M NaCl at pH 7.4 and then admixed with SPDP-activated edestin prepared above under continuous stirring conditions. The degree of coupling of the peptide with edestin was monitored by diluting an aliquot of the mix 1:100 at time zero, and each hour thereafter, and measuring the release of pyridine-2-thione at 343 nm in a spectrophotometer. The end point of coupling was determined to be an increase of 0.2 in absorbency, or upon visualization of precipitate at which point edestin conjugates peptide was formed, and designated cortistatin-14-edestin immunogen.

To prepare antisera specific for the remaining peptides listed in Table 1 and for species-specific preprocortistatin and procortistatin, the protein and peptide preparations described in Example 2 are similarly prepared as immunogens.

2) Immunization and Collection of Polyclonal Antisera

To form anti-peptide antibodies, the cortistatin-14-edestin immunogen prepared above was emulsified using Adjuvant Complete Freund (DIFCO Laboratories, Detroit, Mich.) for the first injection and Adjuvant Incomplete Freund (DIFCO) for all subsequent injections according to the manufacturer's instructions, and the immunogen was incorporated into the emulsion at a concentration of 2 mg/ml. One-half ml of a prepared emulsion was injected subcutaneously into each of two New Zealand white rabbits after pre-immune serum samples are collected. The rabbits were injected three times at weekly intervals following the injection protocol as detailed. Two weeks after the last injection, blood samples were collected to check antibody titer against the specific peptide cortistatin-14-edestin used as an immunogen by the ELISA assay described below in Example 3C. The collected blood samples were stored at 4° C. for 12 hours, after which the samples were centrifuged at 3000×g for 20 minutes. The resultant supernatant containing anti-peptide antibodies was collected, designated polyclonal anti-cortistatin peptide antibodies and stored at −20° C.

Immunization of separate rabbits for the production of antisera against each of the peptides and proteins prepared in Example 2 is performed as described herein. The resultant antisera are then screened by ELISA as described below.

C. ELISA to Screen Antisera Immunoreactivity

The peptide antibody titers and immunospecificity in sera collected from rabbits in Example 3B is determined in binding assays to native cortistatin molecules in tissue preparation (i.e., in situ) as described in the Specification or by an enzyme-linked-immunosorbent-assay (ELISA) as described below. The antigens used in the ELISA include the immunizing peptide as well as recombinant proteins and polypeptides as described in Example 2.

To determine the immunospecificity of the rabbit antisera obtained in Example 2C, ELISA assays are performed. Briefly, 50 l of 50 M concentrations of cortistatin peptides prepared in Example 1 and listed in Table 1 in a buffer consisting of 0.05 M sodium carbonate ($Na_2CO_3$) and 0.02% $NaN_3$ at pH 9.0 are separately admixed into the wells of microtiter plates. The plates are maintained at 37° C. for one hour to permit the antigens to become operatively affixed to the well walls. After washing the antigen-coated wells with TBS, the wells are blocked with 250 l/well of 10% bovine serum albumin (BSA) (Sigma) in TBS for one hour at 22° C. The blocking solution is then removed and the wells are subsequently washed five times with 250 l/well of maintenance buffer (0.05 M Tris-HCl, 0.1 M NaCl, 0.02% $NaN_3$, 1 mg/ml BSA, 5 mM $CaCl_2$, 0.01% Tween 20 at pH 7.4).

Fifty 1 of rabbit nonimmune or specific antiserum serially diluted in maintenance buffer are then admixed to the washed wells to form an immunoreaction admixture, that is maintained for one hour at 37° C. to allow formation of a solid-liquid phase immunoreaction products. The wells are then washed three times with maintenance buffer followed by admixture of 50 l of 1.0 g/ml of secondary antibody (polyclonal biotinylated goat-anti-rabbit-IgG) (Pierce Biohemicals, Rockford, Ill.) diluted in maintenance buffer to each well for the detection of immunoreactant products. The plates are maintained for one hour at 37° C. after which time the secondary antibody solution is removed.

After washing the wells as described above, 50 l of 1.0 g/ml streptavidin-alkaline-phosphatase (Pierce Biochemicals) in maintenance buffer are admixed into each well and maintained for 30 minutes at 37° C. Detection of specific immunoreaction products is obtained by admixture of 150 l/well of 5 mg/ml p-nitrophenylphosphate (PNPP) (Pierce Biochemicals) in 0.1 M diethanolamine and 0.02% $NaN_3$ at pH 9.0 followed by measurement of the change in absorbance at 405 nm over time using the EL312 Microplate Bio-Kinetics Reader and the KinetiCalc Software Program (Biotek Instruments, Inc., VT). Nonspecific binding is considered as the measure absorbance in 10% BSA blocked wells which serve as negative controls without the preceding coating of a specific protein or peptide. Under the described conditions, nonspecific binding never exceeds more than 5% of the specific binding. Rabbit anti-peptide antisera which exhibit immunoreactivity that produced an optical density change at 405 nm using the kinetic program as compared to the immunoreactivity of pre-immune serum toward peptides, is selected for use as an anti-peptide antibody, and also selected for further purification as described in herein.

Rabbit antisera for the other peptide immunogens are similarly screened for immunoreactivity to the respective peptide immunogens. Rabbit antisera which exhibit significant immunoreactivity as compared to the pre-immune sera toward each of the peptide immunogens are further purified and analyzed as described below.

D. Purification of Anti-Cortistatin Peptide Antibodies

Purification of the IgG fraction from rabbit antiserum, which shows significant reactivity towards the immunizing peptides described above is conducted by ammonium-sulfate precipitation (0–45%), followed by purification of IgG on an ion-exchange Mono Q column (Pharmacia LKB, Piscataway, N.J.) connected to a fast protein liquid chromatography (FPLC) system (Pharmacia). For each antiserum, immunoaffinity purification of the pooled immunoreactive IgG-fraction is performed by passing approximately 100 mg of the IgG over a 5 ml column containing 3 mg of species-specific cortistatin coupled to Sepharose 4B (Pharmacia). After a thorough washing of the column with five column volumes of 0.05 M Tris-HCl and 1 M NaCl at pH 7.4 to remove unbound antibodies, the bound IgG is eluted with two column volumes of 0.1 M glycine-HCl at pH 2.5. The eluted protein is monitored by absorbance at 280 nm and the IgG concentrations determined from the extinction coefficient of 13.5. The eluted IgG is immediately dialyzed against TBS-Az, concentrated against 50% sucrose for approximately three to four hours and once more extensively dialyzed against TBS-Az to a final concentration of 3–4 mg/ml.

E. Preparation of Anti-Cortistatin Monoclonal Antibodies

To prepare monoclonal antibodies to the cortistatin proteins and polypeptides prepared in Example 2, immunogens for each are prepared as described above. Balb/c ByJ mice (The Scripps Research Institute, La Jolla, Calif.) are immunized intraperitoneally (i.p.) with 50 g of prepared immunogen in complete Freund's adjuvant (CFA) followed by a second and third immunization using the same immunogen, each about three weeks apart, in incomplete Freund's adjuvant (IFA). The mice receive a boost of 50 g of the prepared peptide intravenously (i.v.) in normal saline four days prior to fusion and a second similar perfusion boost one day later.

The animals so treated are sacrificed and the spleen of each mouse is harvested. A spleen cell suspension is then prepared. Spleen cells are then extracted from the spleen cell suspension by centrifugation for about ten minutes at 1000 rpm, at 23° C. Following removal of the resultant supernatant, the cell pellet is resuspended in 5 ml cold ammonium chloride ($NH_4Cl$) lysing buffer, and is maintained for about 10 minutes.

Ten ml of Dulbecco's Modified Eagle Medium (DMEM) (GIBCO) and HEPES [4-(2-hydroxyethyl)-1-piperidineethanesulfonic acid] buffer are admixed to the lysed cell suspension to form an admixture, and that admixture is centrifuged for about ten minutes at 1000 rpm at 23° C.

After the resultant supernatant is decanted, the pellet is resuspended in 15 ml of DMEM and HEPES and is centrifuged for about ten minutes at 1000 rpm at 23° C. The above procedure is repeated.

The pellet is then resuspended in 5 ml DMEM and HEPES. An aliquot of the spleen cell suspension is then removed for counting. Fusions were accomplished in the following manner using the non-secreting mouse myeloma cell line P3X63Ag 8.653.1, a subclone of line P3x63Ag 8.653 (ATCC 1580). With a myeloma to spleen cell ratio of about 1 to 10 or about 1 to 5, a sufficient quantity of myeloma cells are centrifuged into a pellet, washed twice in 15 ml DMEM and HEPES, and then centrifuged for 10 minutes at 1000 rpm at 23° C.

Spleen cells and myeloma cells are combined in round bottom 15 ml tubes. The cell mixture is centrifuged for ten minutes at 1000 rpm at 23° C. and the supernatant is removed by aspiration. Thereafter, 200 1 of 50 percent (weight per volume) aqueous polyethylene glycol 4000 molecular weight (PEG); (ATCC Baltimore, Md.) at about 37° C. is admixed with the pellet using a 1 ml pipette with vigorous stirring to disrupt the pellet. The cells are then gently mixed for between 15 and 30 seconds. The resultant cell mixture is centrifuged four minutes at 700 rpm.

At about eight minutes from the time of adding the PEG, 5 ml of DMEM plus HEPES buffer are admixed slowly to the pellet, without disturbing the cells. After one minute, the resulting admixture is broken up with a 1 ml pipette and is maintained for an additional four minutes. This admixture is centrifuged for 7 minutes at 1000 rpm. The resultant supernatant is decanted, 5 ml of HT (hypoxanthine/thymidine) medium are slowly admixed to the pellet, and the admixture is maintained undisturbed for five minutes. The pellet is then broken into large chunks and the final cell suspension is placed into T75 flasks (2.5 ml per flask) into which 7.5 ml HT medium is present. The resulting cell suspension is maintained at 37° C. to grow the fused cells. After 24 hours, 10 ml of HT medium are admixed to the flasks followed six hours later by admixture of 0.3 ml of 0.04 mM aminopterin. Forty-eight hours after fusion, 10 ml of HAT (hypoxanthine/aminopterin/thymidine) medium are admixed to the flasks.

Three days after fusion, viable cells are plated out in 96-well tissue culture plates at about $2 \times 10^4$ viable cells per well (768 total wells) in HAT buffer medium as described in Kennett et al., Curr. Top. Microbiol. Immunol., 81:77 (1978). The cells are fed seven days after fusion with HAT medium and at approximately four to five day intervals thereafter as needed with HT medium. Growth is followed microscopically and culture supernatants are collected about two weeks later. The culture supernatants from HAT resistant cultures are subsequently assayed for the presence of respective cortistatin-specific antibody by solid-phase ELISA as described in Example 3C and selected as hybridomas that produce an antibody of this invention.

The anti-cortistatin antibodies are useful in detecting the presence of cortistatin antigen in a human tissue or body sample through the formation of an immunoreaction complex as obtained in binding assays in situ, ELISA methodologies, by immunohistochemical methods including tissue staining and flow cytometry, or by Western blot analysis. In addition, the anti-cortistatin antibodies prepared herein are useful in methods to inhibit the physiological response of cortistatin receptor following occupancy and activation by cortistatin as described below in Example 8.

4. Detection of Cortistatin Nucleic Acids

A. Detection of Cortistatin mRNA

To characterize cortistatin, the distribution of preprocortistatin mRNA was assessed by Northern blot analysis. Total cellular RNA was prepared from homogenized tissues including rat brain, anterior pituitary, adrenal gland, liver, spleen, thymus, ovary and testes, according to the method described by Chirgwin et al., Biochem., 18:5294–5299 (1979). The RNA was enriched for poly(A)+RNA by oligo (dt)-cellulose chromatography as described by Aviv et al., Proc. Natl. Acad. Sci., USA, 69:1408–1412 (1972). Two g of poly(A)+ selected RNA were fractionated by gel electrophoresis and transferred to nitrocellulose. The latter was then hybridized with a labeled cortistatin cDNA probe having the nucleotide sequence (SEQ ID NO 1). Hybridization conditions were essentially as described by Forss-Petter et al., J. Mol. Neurosci., 1:63–75 (1989). A cyclophilin probe described by Danielson et al., DNA, 7:261–267 (1988) was hybridized to the same blot as a control for concentration and integrity of the RNA samples.

The results of the mRNA screening are shown in FIG. 4. A single band of approximately 600 bp was detected in samples prepared from brain but not adrenal gland, liver, spleen, thymus, ovary, testes or anterior pituitary. The result suggests that the rat preprocortistatin clone whose sequence is shown in FIG. 1 is nearly full length.

Based on the limited distribution of preprocortistatin mRNA in brain, the cellular distribution of cortistatin mRNA was determined by in situ hybridization (ISH) on rat brain sections on free-floating sections as previously described by deLecea et al., Mol. Brain Res.,. 25:286–296 (1994). For double ISH, both probes (digoxigenin- and $^{35}$S-labeled) were incubated together on tissue sectins followed by washing and a second incubation of the sections with an anti-digoxigenin Fab fragment conjugated to alkaline phosphatase (1:3000; Boehringer Mannheim, Indianapolis, Ind.) as described by the manufacturer. For combined in situ hybridization-immunohistochemistry, in situ hybridization was performed first. Sections were then equilibrated in PBS, blocked with 4% BSA and incubated with a somatostatin antiserum described by Morrison et al., Brain Res., 262:344–351 (1983) (S309 diluted 1:2000). This antibody recognizes epitopes in the N-terminus of somatostatin-28 and therefore is unlikely to crossreact with cortistatin-14. Cells containing more than 20 silver grains over the cell body were considered positive, and were counted as an average in eight different sections from three different animals.

Signals were detected only in scattered cells throughout the cerebral cortex and hippocampus. of note, no signal was detected in hypothalamus, an important site of somatostatin expression. In the cortex, signals were especially abundant in layers II–III and VI. The visual/temporal cortex displayed about twice as many cortistatin-positive neurons as the somatosensory cortex. In the hippocampus, cortistatin mRNA expression was found in some non-pyramidal cells in the subiculum and in the stratum oriens of the CA1 and CA3 fields, suggesting that cortistatin mRNA might be present in GABAergic interneurons.

To assess this aspect, double in situ hybridization was performed to detect coexpression of cortistatin and $GAD_{65}$/$GAD_{67}$ mRNAs, which encode the synthetic enzymes for GABA as described by Erlander et al., Neuron, 7:91–100 (1991). All cortistatin-expressing cells also contained either $GAD_{65}$ or $GAD_{67}$ mRNA, thus providing evidence for the GABAergic nature of these neurons.

By combined immunohistochemistry and in situ hybridization, cortistatin and somatostatin appear in different populations of interneurons; while cortistatin is selectively expressed in cells of the cerebral cortex and hippocampus, somatostatin-containing neurons have a wider distribution. Moreover, cortistatin and somatostatin can exist in different populations of interneurons, as demonstrated by the limited co-localization of somatostatin immunoreactivity and cortistatin mRNA. In cortical layers II–III, most positive interneurons expressed either somatostatin or cortistatin but not both, although in some other cortical areas (e.g., layer VI of the visual cortex) as many as 40% of cortistatin-positive cells also contained somatostatin-like immunoreactivity. In the hippocampal CA fields, most (>80%) cortistatin-positive cells were also positive for somatostatin immunoreactivity. Cortistatin was not present in the hilus, which was rich in somatostatin-positive cells.

Hybridization to northern blots of mouse tissues revealed the presence of two bands in brain but not liver, kidney or thymus. Two bands were also observed in the human brain sample.

B. Detection of CTG Repeats in Cortistatin

As previously described in Example 1, the rat, human and mouse preprocortistatin cDNAs are characterized by having multiple iterations of the triplet CTG in the nucleotide sequence encoding leucine residues in a portion of the signal sequence. For the rat sequence, six iterations of the trinucleotide CTG repeats are present while in the mouse sequence three CTG repeats are present for encoding leucine. Similarly, for the human sequence four iterations of the CTG repeats are present.

As previously mentioned, triplet expansions have been determined to be the genetic basis for neurological diseases, e.g., myotonic dystrophy as described by Brook et al., Cell, 68:799–808 (1992) and fragile-X syndrome as described by Fu et al., Cell, 67:1047–1058 (1991). In myotonic dystrophy patients who are mildly affected, at least 50 CTG repeats are present. In severely affected individuals, the expansion can exist up to several kilobase pairs. In contrast, in the normal population, the repeat sequence is highly variable ranging from 5 to 27 copies. Individuals with varying severities of fragile-X have been similarly characterized.

Thus, screening for the presence of a region of DNA in which the repeats are present in either normal, underexpansion or overexpansion form can provide a genetic basis for diagnosis for some diseases. The same may be true for cortistatin in that expansion of the region may contribute to the basis for a sleep-related or disease related to cortical activity of the brain. Consequently, one aspect of the present invention is a genetic screening method to determine the nature of the lysine-encoding triplets in a specified region of cortistatin nucleotide sequence. By screening a large number of samples from a population of normal individuals along with those having sleep disturbances or disorders, the range for normal variability can be determined as well as the correlation of repeat length with a disorder and severity thereof.

Therefore, in view of the nucleotide sequence similarity between rat and mouse preprocortistatin as respectively shown in FIGS. 1 and 3, oligonucleotide primer sequences have been designed to allow for positional amplification by polymerase chain reaction (PCR) of target nucleic acid samples. For screening for transcribed cortistatin, the nucleic acid sample is derived from brain tissue biopsy. Alternatively, the designed primers are useful for amplifying genomic DNA obtained from readily available cells, such as peripheral blood leucocytes.

The 5' primers for rat and mouse respectively encode the amino acid residue sequence Gly-Lys-Arg-Pro-Ser-Ala (SEQ ID NO 17) and Gly-Lys-Trp-Pro-Ser-Ala (SEQ ID NO 18). The nucleotide sequence for the 3' primer is the same for rat and mouse sequence encoding the amino acid residue sequence Trp-Trp-His-Glu-Trp-Ala (SEQ ID NO 19) as written in amino terminal to carboxy terminal direction of the cortistatin protein as shown in FIGS. 1 and 3 and in the respective SEQ ID NOs 2 and 5. Preferred nucleotide sequences for primers corresponding to the amino acids in SEQ ID NOs 17, 18 and 19 are respectively 5'GGCAAGCG-GCCGTCAGCC3' (SEQ ID NO 20), 5' GGCAAGTGGT-CAGCC (SEQ ID NO 21) and 5'AGACTCATGCCACCA3' (SEQ ID NO 22).

PCR amplifications are then performed with a sample of nucleic acid according to methods well known to one of ordinary skill in the art and as described in "Current Protocols in Molecular Biology", Ausubel et al., eds, Chapter 15, Wiley & Sons, Inc., New York (1989).

The resultant amplified DNA is then analyzed by gel electrophoresis for the presence of triplet expansions in the region between the two primer pairs, the region of which for rat and mouse are respectively 171 and 159 nucleotides in length. The amplified rat region corresponds to nucleotide positions 51 through 221 in SEQ ID NO 1 and for mouse the corresponding nucleotide positions in SEQ ID NO 4 are from 49 through 207. An increase in the molecular weight of the fragment is indicative of expansion of a selected triplet repeat. To confirm the presence of expansion and/or compression of the region, the PCR fragments are sequenced. Appropriate diagnoses are then readily made.

5. Detection of Cortistatin Protein

A. Receptor Binding Assays

To determine the binding specificity of cortistatin and in view of its similarity to somatostatin, assays to assess the binding of chemically synthesized, linear cortistatin-14 peptide prepared in Example 2 to somatostatin receptors on $GH_4$ pituitary cells were performed.

$GH_4$ cells, obtained from Dr. Kaare M. Gautvik (University of Oslo) or ATCC, were grown in MEM medium with 12% fetal calf serum in 6-well plates at $10^6$ cells/ml. Each well then received $10^6$ cpm/ml of $^{125}I$ somatostatin-14

(NEN, DuPont, Wilmington, Del.) alone or with increasing concentrations of somatostatin-14 peptide (Sigma) or cortistatin-14 peptide (95%, purified by reverse phase HPLC ranging from $10^{-10}$ M to $10^{-6}$ M. Aprotinin and leupetin (Sigma; 2 g/ml) was included as it reduced non-specific binding to 20% of total bound radioactivity. The binding of $^{125}$I somatostatin in the presence of $10^{-7}$ M somatostatin was considered as unspecific binding as described by Schonbrunn et al., *J. Biol. Chem.*, 235:6473–6483 (1978).

As shown in FIG. 5A, both cortistatin-14 (filled circles) and somatostatin-14 (empty circles) effectively displaced $^{125}$I-somatostatin-14 binding in a dose-dependent manner, with an estimated $K_d$ of $5 \times 10^{-9}$ M, very close to that previously reported for somatostatin as described by Schonbrunn et al., *J. Biol. Chem.*, 235:6473–6483 (1978). The combined data from four independent experiments are plotted as mean values Å standard error. As a control, thryoid releasing hormone (TRH) (Calbiochem, La Jolla, Calif.) and vasoactive intestinal peptide (VIP) (Bachem, Switzerland) did not show any displacement of $^{125}$I-somatostatin.

Parallel assays are readily performed with the cortistatin proteins and polypeptides listed in Table 1, prepared by either recombinant or synthetic means as described above.

Comparable binding assays, as described in Example 6, are performed with $GH_4$ cells or cortistatin-specific positive cells or tissues containing such to identify a cortistatin analog, also referred to as a cortistatin receptor ligand.

B. Receptor Activation Assays

To investigate whether cortistatin modulates somatostatin receptor activation, the concentration of cyclic AMP (cAMP) was determined following stimulation of $GH_4$ cells with VIP or TRH in the presence or absence of either cortistatin or somatostatin.

For the cAMP assays, $GH_4$ cells were grown under the same conditions as for the binding assays. The cells were washed with MEM without serum, but containing leupeptin, aprotinin and 1 mM 3-isobutyl-methyl-xantine (IBMX). The cells were pretreated with somatostatin-14 and cortistatin-14 for 15 minutes before VIP at $10^{-6}$ M was added or TRH at $10^{-7}$ M. To each well, $^3$H cyclic AMP was added before the content was removed, to calculate recovery. For cAMP measurements, a RIA kit (Amersham, Arlington Heights, Ill.) was used according to the instructions of the manufacturer. Each time point represents 2–4 replicates and the experiments were carried out twice.

As shown in FIG. 5B, both VIP and TRH at respective concentrations of $10^{-6}$ M and $10^{-7}$ M increased the intracellular concentration of cAMP while the somatostatin and cortistatin peptides at $10^{-6}$ M had no effect as compared to control.

As shown in FIG. 5C, both statin peptides showed indistinguishably effective inhibition of VIP and TRH stimulation of cAMP in cells. Both peptides at $10^{-8}$ M completely inhibited the action of TRH, whereas they attenuated the effect of VIP in a dose-dependent manner by about 50% at $10^{-6}$ M.

Therefore, in view of the results shown in FIGS. 5A–5C, cortistatin appears to act as an agonist on the endogenous somatostatin receptors expressed by $GH_4$ cells, although these cells may express a heterogeneous population of receptors and the agonist activity may not necessarily be its role at its sites of expression. Although a cortistatin-specific receptor has yet been identified, the assays described in Example 7 using the cortistatin proteins and polypeptides listed in Table 1, prepared by either recombinant or synthetic means are designed to facilitate such identification of a cortistatin-specific receptor.

6. Detection of Cortistatin Analogs and Antagonists

The receptor binding and cAMP activation assays described in Example 5 are used in this invention to screen for cortistatin analogs as well as antagonists, the latter of which includes cortistatin-specific antibodies. Anti-cortistatin antibodies that are cortistatin antagonists are also referred to as cortistatin receptor antagonists in that the antibody blocks the binding of the cortistatin ligand to its receptor, thereby preventing receptor occupancy and activation.

In the receptor binding assay, analogs of cortistatin are identified in the same manner as was used to identify cortistatin as an agonist of somatostatin receptors. In a parallel assay, a cortistatin antagonist, such as an anti-cortistatin peptide antibody preparation as described in Example 4, is identified by blocking the cortistatin-14 ability to displace labeled somatostatin from binding to the somatostatin-receptor-bearing cells or to cortistatin-receptor-bearing cells. In a modified receptor binding assay using $^{125}$I-cortistatin-14 or any labeled cortistatin protein or polypeptide of this invention, preferably procortistatin, a cortistatin antagonist can be identified if the candidate molecule is shown to displace the binding of the labeled cortistatin peptide to GH4 cells or cells bearing cortistatin-specific receptors.

Confirmation of a cortistatin antagonist is provided in the cAMP assays by incubation of the molecule with the cortistatin-14 peptide prior to addition of the cAMP activators. A cortistatin antagonist is identified by the measured inhibition of cAMP accumulation in assays performed as described for the data shown in FIG. 5C. Cortistatin analogs are identified by the effective inhibition of cAMP accumulation in parallel to that shown in FIG. 5C.

Further confirmation of the identification of a cortistatin analog or antagonist is provided in the in vitro and in vivo electrophysiological assays as described in Example 8 where the functional physiological responses by cortistatin are distinct from those elicited by somatostatin, the responses of which are dependent upon specific receptor activation.

Cortistatin agonists are also identified by their binding patterns on rat brain cryosections, as has been described for somatostatin by Pelletier et al., *Meth. Enzymol.*, 124:607–615 (1986), the disclosure of which is hereby incorporated by reference.

7. Detection of Cortistatin-Specific Receptor

For identifying a cortistatin-specific receptor in the brain, cortistatin-specific binding sites are detected as described by Tran et al., *Eur. J. Pharmacol.*, 101:307–309 (1984), the disclosure of which is hereby incorporated by reference. Briefly, synthetic analogs of cortistatin presented in single-letter code, (YPCKNFFWKTFSSCK (SEQ ID NO 23) or PCKNFFYKTFSSCK (SEQ ID NO 24)), are labeled with $^{125}$I several methods and purified by reverse phase HPLC. Different amounts of $^{125}$I-labeled cortistatin analogs are then incubated with rat brain cryosections in the presence of $10^{-6}$ M cold competitive analog.

Alternatively, tritiated analogs are synthesized and used for in situ autoradiography.

Cortistatin-specific receptors are also identified by binding labeled cortistatin analogs, that include cortistatin proteins and polypeptides listed in Table 1, prepared by either recombinant or synthetic means as described above, to biochemical membrane preparations from cortex. Synthetic cortistatin is immobilized to activated agarose columns (such as BioGel 10 columns from BioRad) and used to purify cortistatin-binding proteins from brain extracts. Such methods are well known in the art.

8. Physiology of Cortistatin and Therapeutic Methods

Somatostatin is known to hyperpolarize central neurons by increasing potassium conductances as described by Inoue et al., *J. Physiol.*, 407:177–198 (1988), including the voltage-dependent potassium M current (see Moore et al., *Science*, 239:278–280 (1988) and Jacquin et al., *Proc. Natl. Acad. Sci., USA*, 85:948–952 (1988)). To complete the characterization of the physiological role of cortistatin, assays were performed to determine whether cortistatin had somatostatin-like effects on hippocampal neurons by means of current- and voltage-clamp recordings in the hippocampal slice preparation.

Intracellular recordings were obtained in rat hippocampal slices using sharp glass micropipettes as previously described by Schweitzer et al., *J. Neurosci.*, 13:2033–2049 (1993). Recordings were made from 11 hippocampal CA1 pyramidal cells with an average resting membrane potential of −70 Å 1 mV (mean Å s.e.m.) and action potential of 103 Å 2 mV. Current-clamp recording of a CA1 neuron manually depolarized to −65 mV (resting membrane potential was −70 mV) to elicit action potential firing (upward deflections, truncated) is shown in FIG. 6A.

Superfusion of 1 M cortistatin-14 peptide (bar above record), prepared as described in Example 3, like somatostatin-14, hyperpolarized these neurons (10 of 11 cells), in association with inhibition of action potential firing, followed by recovery to control levels upon washout of the peptide. Unlike somatostatin, the cortistatin-14-mediated effect developed slowly, reaching a maximum steady effect six to eight minutes after the onset of the response. This contrasted with the time-to-peak of somatostatin's effect on these neurons under the same experimental conditions that was much shorter (2–3 minutes).

To determine the mechanism of the cortistatin-induced inhibition, we assessed the effect of cortistatin on the M current ($I_M$), a non-inactivating voltage-dependent potassium current seen in hippocampal neurons as described by Halliwell et al., *Brain Res.*, 250:71–92 (1982).

In voltage clamp assays, the $I_M$ relaxation was observed by applying hyperpolarizing steps (5 to 25 mV) from a holding potential of −43 to −48 mV. FIG. 6B shows the voltage-clamp recording of a CA1 neuron held at −43 mV; an $I_M$ relaxation was evoked with 10 mV hyperpolarizing step.

As previously described for somatostatin (Moore et al., *Science*, 239:278–280 (1988) and Schweitzer et al., *Nature* 346:464–466 (1990)), cortistatin-14 (1 M, 7 minutes) superfusion increased the amplitude of the $I_M$ relaxation by 60% (see arrows) concomitantly with an outward steady-state current, as shown in FIG. 6B with the dotted line as control holding current, with recovery to control levels upon washout.

The inhibitory effects of cortistatin on the excitability of CA1 pyramidal neurons as viewed by population spike (PS) amplitudes was paralleled in vivo in the anesthetized preparation. For the in vivo studies, male Sprague-Dawley rats were anesthetized with halothane (0.9–1.1%). The commisural pathway was stimulated and elicited field potentials in the CA1 region essentially as described by Steffensen et al., *Brain Res.*, 538:46–53 (1991). Cortistatin (1 mg/ml) was dissolved in saline and administered iontophoretically through one barrel of a multibarreled micropipette. As shown in FIG. 6C, stimulus-response curves were generated and the PS amplitude was monotonically related to stimulus intensity tested at three response levels: threshold, half-maximal and maximal (control mean half-maximal PS amplitude=4.7 mV Å 0.5; n=5). Asterisks represent significance levels at P<0.05. The data was compiled with software (LabView Instruments, National Instruments, Austin, Tex.) as described by Steffensen et al., *Brain Res.*, 538:46–53 (1991).

Stimulation of the monosynaptic afferent input to the CA1 region evoked a characteristic population spike (PS) that represents the synchronous firing of pyramidal cells, superimposed on a field synaptic potential waveform as described by Anderson et al., *Exp. Brain Res.*, 13:208–221 (1971). As is apparent in FIG. 6C, microiontophoretic application of cortistatin, like somatostatin, significantly decreased PS amplitudes both at half-maximal and maximal levels of stimulation.

As cortistatin is expressed in interneurons located in the cerebral cortex and hippocampus, its effects on cortical measures of neuronal excitability was next determined in vivo. Up to 6 nmoles of HPLC-purified synthetic cortistatin-14 peptide prepared in Example 3 were infused into the brain ventricles of rats (n=5) and recorded the electroencephalogram (EEG) for four hours after peptide injection. In addition, rats were observed for changes in spontaneous behavior through a one-way window. Standard methodologies for chronic electrophysiological preparation and data acquisition were used. Procedures for EEG recordings and PP studies are as described by Prospero-Garcia et al., *Pharmacol. Biochem. Behav.*, 49:413 (1994) and Steffensen et al., *Brain Res.*, 652:149 (1994).

FIGS. 7A-1, 7A-2, 7A-3 and 7A-4 show the effects of the intracerebroventricular administration of cortistatin on the sleep-wake cycle of the rat. FIGS. 7A-1, 7A-2, 7A-3 and 7A-4 respectively illustrate wakefulness, slow-wave sleep 1, slow-wave sleep 2 and REM sleep. The effects of the sleep cycle were assessed with cortistatin-14 dosages at 100 ng, 500 ng, 1 g and 10 g as plotted from left to right in the bar graphs as shown against saline control. Asterisks represent significance levels of P<0.05; ANOVA.

Cortistatin-14-peptide-treated animals demonstrated a clear hypoactive behavior compared to the saline-injected rats, but kept their eyes open and displayed other signs of wakefulness for a short period of time (15–20 minutes). In these animals, the EEG showed a dramatic increase in cortical slow waves (1–4 Hz). As shown by referring to FIGS. 7A-1 through 7A-4, polygraphic monitoring of arousal states subsequent to the administration of cortistatin also indicated that rats spent up to 75% of the four hour recording time in slow-wave sleep compared to 40% in saline-treated control animals. A significant reduction on paradoxical (REM) sleep was also observed with the highest dose of cortistatin, in clear contrast to the reported increase in REM sleep after administration of a similar dose of somatostatin as described by Danguir et al., *Brain Res.*, 367:26–30 (1986).

In addition, two doses of cortistatin (0.1 and 1 g) were tested in reversed sleep cycle rats (n=7/group). Since in this model the animals have already achieved their physiological demand of sleep as described by Inoue et al., *Neurosci. Lett.*, 49:207–209 (1984), the efficiency of cortistatin as a sleep-inducing molecule would be more evident. Cortistatin significantly decreased wakefulness (49.1 Å 2% in saline-treated control rats; 31 Å 2.6% with 100 ng of cortistatin; 32 Å 8.78% with 1 g) and increased slow wave sleep 2 (35.8 Å 1.8% in controls; 51.5 Å 3.8% with 100 ng; 53.7 Å 7.3% with 1 g) but did not significantly affect slow wave sleep 1 (8.8 Å 1.7% in control rats; 8.1 Å 0.9% with 100 ng; 5.6 Å 1.4% for 1 g) or REM sleep (6.2 Å 1.4% in controls; 9.3 Å 1.7% with 100 ng; 7.7 Å 1.3% with 1 g). These results strongly support the discovery of the present invention that cortistatin is a sleep-modulating substance.

To investigate the mechanisms by which cortistatin might facilitate cortical slow waves and reduce the duration of REM sleep, the possibility that cortistatin produced these effects, in part, by modulating acetylcholine (ACh) activity as described by Steriade et al., *Ann. Rev. Pharmacol. Toxicol.*, 27:137–156 (1987) was investigated. The interactions between cortistatin and ACh on hippocampal CA1 neurons was examined using an evoked paired-pulse (PP) stimulation paradigm to test feed-forward and feed-back inhibitory processes mediated in part by hippocampal interneurons (see Andersen et al., *J. Neurophysiol.*, 27:607–619 (1964) and Kandel et al., *J. Neurophysiol.*, 24:243–259 (1961).

The effects of iontophoretically applied ACh (0.9 M), somatostatin (1.5 mM) and cortistatin on PP responses in CA1 neurons in vivo are shown in FIG. 7B. Stimulation intensity was adjusted after drug treatment to achieve control PS amplitudes before performing PP studies.

Without ACh, stimulation at half-maximal stimulus levels revealed a characteristic biphasic PP response curve as described by Steffensen et al., *Brain Res.*, 538:46–53 (1991). Microiontophoretic application of ACh significantly antagonized the typical inhibitory phase of PP responses seen at interstimulus intervals from 60–80 msec (asterisks correspond to a signficance level of P<0.05; see FIG. 7B; data from 80 msec intervals are shown in FIGS. 7C–E). FIGS. 7C–7F each representative recordings of field potentials elicited in CA1 by commisural stimulation. In the baseline recordings shown in FIG. 7C (calibration bars: 2 mV and 10 ms), the second response is completely inhibited at this interstimulus interval (80 ms). Iontophoretic administration of ACh reduced PP inhibition as shown in FIG. 7D. This effect was antagonized by the simultaneous application of cortistatin shown in FIG. 7E. In FIG. 7F, somatostatin markedly decreased PP inhibition (calibration bar 1 mV and 10 ms).

To summarize, cortistatin itself (not shown) had no significant effects on PP responses in CA1 but as shown in FIG. 7E, completely antagonized the effects of ACh (P<0.05). The effects of somatostatin on PP responses were similar to those of ACh (FIG. 7B; data from 80 msec shown in FIG. 7F) but were significantly different from those of cortistatin (asterisks correspond to significance levels of P<0.05).

To investigate further whether cortistatin also interacts with cholinergic systems that regulate cortical function, the effects of cortistatin on ACh-induced desynchronization of EEG in the cerebral cortex of anesthetized rats was determined. Thus, ACh and cortistatin was microiontophoretically (100–250 nA) applied on local EEG activity recorded in the visual cortex. For the data shown in FIG. 7G, the results from the experimental groups were derived from averaged EEG spectral activity determinations and expressed as means Å s.e.m. (Asterisk represents significance levels P<0.05 from baseline; two asterisks represent significance levels P<0.05 from ACh; ANOVA).

As shown in FIG. 7G, electrophoretic application of ACh markedly desynchronized the local EEG by increasing the potency of the theta (4.5–8 Hz) and beta (13–20 Hz) bands, i.e., increased the averaged EEG power spectra (four second epochs over three minutes) in the 8–16 Hz frequency band range. In contrast, the averaged EEG during infusion of cortistatin alone or ACh and cortistatin combined were not different from baseline recordings of slow waves of 0.5–4 Hz. The effect of Ach was effectively prevented by the simultaneous electrophoretic application of cortistatin-14 peptide that antagonized the increase in fast frequency activity produced by Ach alone.

To further the diagnostic and therapeutic methods of this invention, the electrophysiological assays described herein are also performed with the other cortistatin proteins and polypeptides listed in Table 1, prepared by either recombinant or synthetic means as described above. In addition, the anti-cortistatin antibodies of this invention are useful in in vitro assays as well as in vivo applications as described above to facilitate the therapeutic amelioration of a sleep disorder, such as narcolepsy, as the anti-cortistatin antibodies prevent activation of cortistatin receptor by binding cortistatin.

9. Analysis of Structural and Functional Characteristics of Cortistatin with Somatostatin The present invention describes the discovery and isolation of a cDNA clone of a mRNA that encodes the precursor of a novel member of the somatostatin family whose distribution is primarily restricted to GABAergic cortical interneurons. GABAergic neurons have been shown to finely modulate the output of principal neurons of the cerebral cortex and hippocampus as described by Buhl et al., *Nature* 368:823–828 (1994), areas that have been implicated in arousal state and complex cognitive functions, including learning and memory (see Wilson et al., *Science*, 265:676–679 (1994). Cortistatin may therefore play a role in elaborating these functions.

The peptides, cortistatin-14 and somatostatin-14, appear to have similar effects on the physiology of hippocampal neurons. As shown in the Examples above, both peptides bind to somatostatin receptors on $GH_4$ cells with very similar affinities, inhibit the hormonally-induced accumulation of cAMP in these cells with similar efficiencies, cause neuronal hyperpolarization and increase the M-current in hippocampal neurons, thus suggesting that they could act through the same receptors in vivo. The presence of the common amino acid residues FWKT (SEQ ID NO 2 from position 104 to 107), that have been shown to be critical for somatostatin binding, also supports the idea of cortistatin binding to somatostatin receptors.

Nevertheless, cortistatin's effects on the activity of hippocampal neurons in vivo and on sleep physiology are clearly distinct from those of somatostatin. Thus, cortistatin could differentially bind to somatostatin receptor subtypes different from the ones analyzed here, or it could act on-opioid receptors, as has been demonstrated for the somatostatin analog octeotride and the receptor antagonist CTOP as described by Maurer et al., *Proc. Natl. Acad. Sci., USA,* 79:4815–4817 (1982). Cortistatin and somatostatin co-exist in some interneurons in the deep cortical layers and hippocampus, thus suggesting that these statins may compete for the same receptors, or they may be released from different synaptic boutons in response to different stimuli.

Cortistatin appears to be an inhibitory neuromodulator in the hippocampus. The hyperpolarization seen in current-clamp recordings is likely to be due, at least in part, to the augmentation of the non-inactivating potassium M-current. However, as with somatostatin, another $K^{30}$ channel mechanism could also participate in the cortistatin-induced inhibitory effect (see Schweitzer et al., *J. Neurosci.*, 13:2033–2049 (1993). Indeed the delayed effects seen in the hippocampal slice, along with the observed differences in functional responses, may suggest a distinct, uncharacterized cortistatin receptor. In binding studies to cloned somatostatin receptors, cortistatin exhibited affinity comparable to somatostatin for somatostatin receptor 1 (SSTR1), but far lesser affinity for SSTR 2–5. Since SSTR3 and 4 are the predominant SSTRs in the brain regions in which cortistatin is expressed, the existence of an uncharacterized receptor is favored. Alternatively, the delayed effects could merely indicate a more avid uptake, degradation or more limited access to slice tissue due to an additional positive charge present in cortistatin, compared to somatostatin. These factors could require longer-term saturation and prolonged superfusion before significant receptor activation could occur.

The administration of cortistatin into the brain ventricles induced a marked enhancement of slow-wave sleep and decreased the REM phase in a dose-dependent manner. These effects are opposite to those described for somatostatin, which facilitates REM sleep generation as described by Danguir et al., *Brain Res.*, 367:26–30 (1986). Moreover, the behavior exhibited by cortistatin-treated rats was clearly different from the characteristic behaviors (i.e. hypermotility, barrel rotation) previously described for somatostatin-treated rats (see, Rezek et al., *Pharmacol. Biochem. Behavior*, 5:73–77 (1976) and Vecsei et al., *Peptides*, 10:1153–1157 (1989). The data provided herein indicating that cortistatin enhances slow-wave sleep and reduces REM sleep suggest that the effects of cortistatin are produced, in part, by modulating cholinergic function.

Induction of slow-wave sleep is characterized by the appearance of slow frequency waves in cortical activity and the reduction of ACh availability in the cerebral cortex, as shown in several preparations (see Kodama et al., *Neurosci. Lett.*, 114:277–282 (1990) and Marrosu et al., *Brain Res.*, 671:329–332 (1995). Recent electrophysiological studies in vivo have shown that the expression of slow-wave sleep in the rat cerebral cortex coincides with an increase in paired-pulse inhibition in the hippocampal CA1 region as described by Prospero-Garcia et al., *Neurosci. Lett.*, 156:158–162 (1993). By contrast, during active wakefulness and REM sleep there is a marked reduction in PP inhibition, when the availability of ACh is much higher. The lack of effect of cortistatin on PP inhibition contrasts with the potent inhibitory effect of somatostatin on this measure observed in the present invention, which is supported by the somatostatin reduction of GABA-mediated synaptic potentials in CA1 pyramidal neurons previously reported by Scharfman et al., *Brain Res.*, 493:205–211 (1989).

Together, this provides another functional difference between cortistatin and somatostatin. These results are consistent with those in reverse-phased and awake rats, where cortistatin markedly reduced the duration of cortical electrical activity that is associated with the cholinergic system, as well as the ACh-induced desynchronization of local EEG. Therefore, cortistatin antagonizes the effects of ACh in both the hippocampus and the cerebral cortex in vivo. The findings reported here thus provide the physiological basis that this novel neuropeptide, cortistatin, functions as a regulator of neuronal activity and sleep. As such, cortistatin, analogs and antagonists thereof, are valuable reagents in use in the diagnostic and therapeutic methods of this invention.

The foregoing specification, including the specific embodiments and examples, is intended to be illustrative of the present invention and is not to be taken as limiting. Numerous other variations and modifications can be effected without departing from the true spirit and scope of the invention.

What is claimed is:

1. An isolated and purified antibody which binds to a protein having cortistatin-like activity wherein said protein is selected from the group consisting of SEQ ID NO: 23, SEQ ID NO: 24, SEQ ID NO: 26, positions 44 to 74 of SEQ ID NO: 26, and positions 77 to 105 of SEQ ID NO: 26.

2. The antibody of claim 1, wherein the antibody is free from immunoreaction with neuropeptides other than cortistatin.

3. The antibody of claim 1, wherein the antibody is a monoclonal antibody.

4. An immunologically active fragment of an antibody of claim 1 selected from the group consisting of a Fab, Fab', F(ab')$_2$ and F(v) fragment.

5. A method of making an antibody of claim 1, comprising the steps of:

(i) immunizing a mammal with an inoculum containing an immunologically effective amount of a cortistatin polypeptide to induce in the mammal antibody molecules having immunospecificity to the cortistatin polypeptide;

(ii) collecting the antibody molecules; and (iii) isolating the antibody molecules that have immunospecificity to the cortistatin polypeptide.

6. A method of making an antibody of claim 3, comprising the steps of:

(i) initiating a monoclonal hybridoma culture with a nutrient medium containing a hybridoma that produces and secretes antibody molecules with cortistatin specificity;

(ii) maintaining the culture under conditions and for a time period sufficient for the hybridoma to secrete the antibody molecules into the medium;

(iii) collecting the antibody-containing medium; and (iv) isolating the antibody molecules that have cortistatin specificity.

7. A hybridoma cell that produces a monoclonal antibody of claim 3.

8. A pharmaceutical composition comprising an antibody of claim 1 and a pharmaceutically acceptable adjuvant.

* * * * *

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
      (A) LENGTH: 438 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: CDS
      (B) LOCATION: 30..368

(xi) SEQUENCE DESCRIPTION: SEQ ID NO: 1:

```
AAAGCACAGA CTTCAGGTTT CCAAGGAGG ATG GGT GGC TGC AGC ACA AGA GGC      53
                                Met Gly Gly Cys Ser Thr Arg Gly
```

-continued

```
                    1               5
AAG CGG CCG TCA GCC CTC AGT CTG CTG CTG CTG CTG CTC TCG GGG         101
Lys Arg Pro Ser Ala Leu Ser Leu Leu Leu Leu Leu Leu Ser Gly
     10              15                  20

ATC GCA GCC TCT GCC CTC CCC CTG GAG AGC GGT CCC ACC GGC CAG GAC     149
Ile Ala Ala Ser Ala Leu Pro Leu Glu Ser Gly Pro Thr Gly Gln Asp
 25          30                  35                      40

AGT GTG CAG GAT GCC ACA GGC GGG AGG AGG ACC GGC CTT CTG ACT TTC     197
Ser Val Gln Asp Ala Thr Gly Gly Arg Arg Thr Gly Leu Leu Thr Phe
                 45                  50                  55

CTT GCC TGG TGG CAT GAG TGG GCT TCC CAA GAC AGC TCC AGC ACC GCT     245
Leu Ala Trp Trp His Glu Trp Ala Ser Gln Asp Ser Ser Ser Thr Ala
             60                  65                  70

TTC GAA GGG GGT ACC CCG GAG CTG TCT AAG CGG CAG GAA AGA CCA CCC     293
Phe Glu Gly Gly Thr Pro Glu Leu Ser Lys Arg Gln Glu Arg Pro Pro
         75                  80                  85

CTC CAG CAG CCC CCA CAC CGG GAT AAA AAG CCC TGC AAG AAC TTC TTC     341
Leu Gln Gln Pro Pro His Arg Asp Lys Lys Pro Cys Lys Asn Phe Phe
     90                  95                  100

TGG AAA ACC TTC TCC TCG TGC AAG TAGCCCGAGC CTGACCGGAG CCTGACCGGC    395
Trp Lys Thr Phe Ser Ser Cys Lys
105                 110

CACCCTGTGA ATGCAGCCGT GGCCTGAATA AAGAGTGTCA AGT                    438

(2) INFORMATION FOR SEQ ID NO: 2:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO: 2:

Met Gly Gly Cys Ser Thr Arg Gly Lys Arg Pro Ser Ala Leu Ser Leu
 1               5                  10                  15

Leu Leu Leu Leu Leu Leu Ser Gly Ile Ala Ala Ser Ala Leu Pro Leu
             20                  25                  30

Glu Ser Gly Pro Thr Gly Gln Asp Ser Val Gln Asp Ala Thr Gly Gly
         35                  40                  45

Arg Arg Thr Gly Leu Leu Thr Phe Leu Ala Trp Trp His Glu Trp Ala
     50                  55                  60

Ser Gln Asp Ser Ser Ser Thr Ala Phe Glu Gly Gly Thr Pro Glu Leu
 65                  70                  75                  80

Ser Lys Arg Gln Glu Arg Pro Pro Leu Gln Gln Pro Pro His Arg Asp
                 85                  90                  95

Lys Lys Pro Cys Lys Asn Phe Phe Trp Lys Thr Phe Ser Ser Cys Lys
             100                 105                 110

(2) INFORMATION FOR SEQ ID NO: 3:

(i) SEQUENCE CHARACTERISTICS:
        (A) LENGTH: 110 amino acids
        (B) TYPE: amino acid
        (D) TOPOLOGY: linear (ii) MOLECULE TYPE: protein (v) FRAGMENT TYPE: C-terminal (xi) SEQUENCE DESCRIPTION: SEQ ID NO: 3:
```

```
Gln Cys Ala Leu Ala Ala Leu Cys Ile Val Leu Ala Leu Gly Gly Val
  1               5                  10                  15

Thr Gly Ala Pro Ser Asp Pro Arg Leu Arg Gln Phe Leu Gln Lys Ser
             20                  25                  30

Leu Ala Ala Ala Thr Gly Lys Gln Glu Leu Ala Lys Tyr Phe Leu Ala
         35                  40                  45

Glu Leu Leu Ser Glu Pro Asn Gln Thr Glu Asn Asp Ala Leu Glu Pro
 50                  55                  60

Glu Asp Leu Pro Gln Ala Ala Glu Gln Asp Glu Met Arg Leu Glu Leu
 65                  70                  75                  80

Gln Arg Ser Ala Asn Ser Asn Pro Ala Met Ala Pro Arg Glu Arg Lys
             85                  90                  95

Ala Gly Cys Lys Asn Phe Phe Trp Lys Thr Phe Thr Ser Cys
            100                 105                 110

(2) INFORMATION FOR SEQ ID NO: 4:

(i) SEQUENCE CHARACTERISTICS:
        (A) LENGTH: 427 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 25..354

(xi) SEQUENCE DESCRIPTION: SEQ ID NO: 4:

GCACGAGGCT CAGCACGTCC GAGG ATG ATG GGT GGC CGA GGC ACA GGA GGC        51
                          Met Met Gly Gly Arg Gly Thr Gly Gly
                            1               5

AAG TGG CCC TCA GCC TTC GGG CTG CTG CTG CTC TGG GGG GTC GCA GCC       99
Lys Trp Pro Ser Ala Phe Gly Leu Leu Leu Leu Trp Gly Val Ala Ala
 10                  15                  20                  25

TCC GCC CTT CCC CTG GAG AGT GGC CCT ACT GGC CAG GAC AGT GTG CAG      147
Ser Ala Leu Pro Leu Glu Ser Gly Pro Thr Gly Gln Asp Ser Val Gln
             30                  35                  40

GAA GCC ACC GAG GGG AGG AGC GGC CTT CTG ACT TTC CTT GCC TGG TGG      195
Glu Ala Thr Glu Gly Arg Ser Gly Leu Leu Thr Phe Leu Ala Trp Trp
         45                  50                  55

CAC GAG TGG GCT TCC CAA GCC AGC TCC AGC ACC CCC GTC GGA GGG GGT      243
His Glu Trp Ala Ser Gln Ala Ser Ser Ser Thr Pro Val Gly Gly Gly
         60                  65                  70

ACC CCC GGG CTG TCC AAG AGC CAG GAA AGG CCA CCC CCC CAA CAG CCC      291
Thr Pro Gly Leu Ser Lys Ser Gln Glu Arg Pro Pro Pro Gln Gln Pro
 75                  80                  85

CCA CAC CTG GAT AAA AAG CCC TGC AAG AAC TTC TTC TGG AAA ACC TTC      339
Pro His Leu Asp Lys Lys Pro Cys Lys Asn Phe Phe Trp Lys Thr Phe
 90                  95                 100                 105

TCC TCG TGC AAG TAACCCCACC CTGGGCATAG CACCCTGGCC ACCCTGTGAG          391
Ser Ser Cys Lys
            110

ATGCCAACGA GACCTGAATA AAGACTGTCA ATCAAC                              427

(2) INFORMATION FOR SEQ ID NO: 5:
```

(i) SEQUENCE CHARACTERISTICS:
    (A) LENGTH: 109 amino acids
    (B) TYPE: amino acid
    (D) TOPOLOGY: linear (ii) MOLECULE TYPE: protein (xi) SEQUENCE DESCRIPTION: SEQ ID NO: 5:

Met Met Gly Gly Arg Gly Thr Gly Gly Lys Trp Pro Ser Ala Phe Gly
1               5                   10                  15

Leu Leu Leu Leu Trp Gly Val Ala Ala Ser Ala Leu Pro Leu Glu Ser
            20                  25                  30

Gly Pro Thr Gly Gln Asp Ser Val Gln Glu Ala Thr Glu Gly Arg Ser
        35                  40                  45

Gly Leu Leu Thr Phe Leu Ala Trp Trp His Glu Trp Ala Ser Gln Ala
    50                  55                  60

Ser Ser Ser Thr Pro Val Gly Gly Thr Pro Gly Leu Ser Lys Ser
65                  70                  75                  80

Gln Glu Arg Pro Pro Pro Gln Pro Pro His Leu Asp Lys Lys Pro
                85                  90                  95

Cys Lys Asn Phe Phe Trp Lys Thr Phe Ser Ser Cys Lys
            100                 105

(2) INFORMATION FOR SEQ ID NO: 6:

(i) SEQUENCE CHARACTERISTICS:
        (A) LENGTH: 85 amino acids
        (B) TYPE: amino acid
        (D) TOPOLOGY: linear (ii) MOLECULE TYPE: protein (v) FRAGMENT TYPE: C-terminal (xi) SEQUENCE DESCRIPTION: SEQ ID NO: 6:

Ser Ala Leu Pro Leu Glu Ser Gly Pro Thr Gly Gln Asp Ser Val Gln
1               5                   10                  15

Asp Ala Thr Gly Gly Arg Arg Thr Gly Leu Leu Thr Phe Leu Ala Trp
            20                  25                  30

Trp His Glu Trp Ala Ser Gln Asp Ser Ser Ser Thr Ala Phe Glu Gly
            35                  40                  45

Gly Thr Pro Glu Leu Ser Lys Arg Gln Glu Arg Pro Pro Leu Gln Gln
    50                  55                  60

Pro Pro His Arg Asp Lys Lys Pro Cys Lys Asn Phe Phe Trp Lys Thr
65                  70                  75                  80

Phe Ser Ser Cys Lys
            85

(2) INFORMATION FOR SEQ ID NO: 7:

(i) SEQUENCE CHARACTERISTICS:
        (A) LENGTH: 29 amino acids
        (B) TYPE: amino acid
        (D) TOPOLOGY: linear (ii) MOLECULE TYPE: protein (v) FRAGMENT TYPE: C-terminal (xi) SEQUENCE DESCRIPTION: SEQ ID NO: 7:

Gln Glu Arg Pro Pro Leu Gln Gln Pro Pro His Arg Asp Lys Lys Pro
1               5                   10                  15

```
Cys Lys Asn Phe Phe Trp Lys Thr Phe Ser Ser Cys Lys
            20                  25
```

(2) INFORMATION FOR SEQ ID NO: 8:

(i) SEQUENCE CHARACTERISTICS:
        (A) LENGTH: 14 amino acids
        (B) TYPE: amino acid
        (D) TOPOLOGY: linear (ii) MOLECULE TYPE: protein (v) FRAGMENT TYPE: C-terminal (xi) SEQUENCE DESCRIPTION: SEQ ID NO: 8:

```
Pro Cys Lys Asn Phe Phe Trp Lys Thr Phe Ser Ser Cys Lys
1               5                   10
```

(2) INFORMATION FOR SEQ ID NO: 9:

(i) SEQUENCE CHARACTERISTICS:
        (A) LENGTH: 13 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 9:

```
Gln Glu Arg Pro Pro Leu Gln Gln Pro Pro His Arg Asp
1               5                   10
```

(2) INFORMATION FOR SEQ ID NO: 10:

(i) SEQUENCE CHARACTERISTICS:
        (A) LENGTH: 84 amino acids
        (B) TYPE: amino acid
        (D) TOPOLOGY: linear (ii) MOLECULE TYPE: protein (v) FRAGMENT TYPE: C-terminal (xi) SEQUENCE DESCRIPTION: SEQ ID NO: 10:

```
Ser Ala Leu Pro Leu Glu Ser Gly Pro Thr Gly Gln Asp Ser Val Gln
1               5                   10                  15

Glu Ala Thr Glu Gly Arg Ser Gly Leu Leu Thr Phe Leu Ala Trp Trp
            20                  25                  30

His Glu Trp Ala Ser Gln Ala Ser Ser Thr Pro Val Gly Gly Gly
            35                  40                  45

Thr Pro Gly Leu Ser Lys Ser Gln Glu Arg Pro Pro Gln Gln Pro
    50                  55                  60

Pro His Leu Asp Lys Lys Pro Cys Lys Asn Phe Phe Trp Lys Thr Phe
65              70                  75                  80

Ser Ser Cys Lys
```

(2) INFORMATION FOR SEQ ID NO: 11:

(i) SEQUENCE CHARACTERISTICS:
        (A) LENGTH: 29 amino acids
        (B) TYPE: amino acid
        (D) TOPOLOGY: linear (ii) MOLECULE TYPE: protein (v) FRAGMENT TYPE: C-terminal (xi) SEQUENCE DESCRIPTION: SEQ ID NO: 11:

Gln Glu Arg Pro Pro Pro Gln Gln Pro Pro His Leu Asp Lys Lys Pro
1               5                   10                  15

Cys Lys Asn Phe Phe Trp Lys Thr Phe Ser Ser Cys Lys
            20                  25

(2) INFORMATION FOR SEQ ID NO: 12:

(i) SEQUENCE CHARACTERISTICS:
        (A) LENGTH: 13 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 12:

Gln Glu Arg Pro Pro Pro Gln Gln Pro Pro His Leu Asp
1               5                   10

(2) INFORMATION FOR SEQ ID NO: 13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 13:

ATCGAGATCT AAGGAGGATG GGTGGCTGCA G                                          31

(2) INFORMATION FOR SEQ ID NO: 14:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 14:

ACTGTCTAGA TCATAGGTCT TCTTCTGATA TTAGTTTTTG TTCCTTGCAC GAGGAGAAGG            60

TTTTCCAG                                                                    68

(2) INFORMATION FOR SEQ ID NO: 15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 15:

ATCGAGATCT GCCCTCCCCC TGGAGA                                26

(2) INFORMATION FOR SEQ ID NO: 16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 16:

ACTGAATTCA GGCCACGGCT GCATTCACAG                            30

(2) INFORMATION FOR SEQ ID NO: 17:

(i) SEQUENCE CHARACTERISTICS:
        (A) LENGTH: 6 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 17:

Gly Lys Arg Pro Ser Ala
1               5

(2) INFORMATION FOR SEQ ID NO: 18:

(i) SEQUENCE CHARACTERISTICS:
        (A) LENGTH: 6 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 18:

Gly Lys Trp Pro Ser Ala
1               5

(2) INFORMATION FOR SEQ ID NO: 19:

(i) SEQUENCE CHARACTERISTICS:
        (A) LENGTH: 6 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 19:

Trp Trp His Glu Trp Ala
1               5

(2) INFORMATION FOR SEQ ID NO: 20:

```
    (i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 20:

GGCAAGCGGC CGTCAGCC                                                          18

(2) INFORMATION FOR SEQ ID NO: 21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 21:

GGCAAGTGGC CCTCAGCC                                                          18

(2) INFORMATION FOR SEQ ID NO: 22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 22:

AGCCCACTCA TGCCACCA                                                          18

(2) INFORMATION FOR SEQ ID NO: 23:

(i) SEQUENCE CHARACTERISTICS:
        (A) LENGTH: 15 amino acids
        (B) TYPE: amino acid
        (D) TOPOLOGY: linear (ii) MOLECULE TYPE: protein (v) FRAGMENT TYPE: C-terminal (xi) SEQUENCE DESCRIPTION: SEQ ID NO: 23:

Tyr Pro Cys Lys Asn Phe Phe Trp Lys Thr Phe Ser Ser Cys Lys
1               5                   10                  15

(2) INFORMATION FOR SEQ ID NO: 24:

(i) SEQUENCE CHARACTERISTICS:
        (A) LENGTH: 14 amino acids
        (B) TYPE: amino acid
        (D) TOPOLOGY: linear
```

(ii) MOLECULE TYPE: protein (v) FRAGMENT TYPE: C-terminal (xi) SEQUENCE DESCRIPTION: SEQ ID NO: 24:

```
Pro Cys Lys Asn Phe Phe Tyr Lys Thr Phe Ser Ser Cys Lys
1               5                   10
```

(2) INFORMATION FOR SEQ ID NO: 25:

(i) SEQUENCE CHARACTERISTICS:
        (A) LENGTH: 701 base pairs
        (B) TYPE: nucleic acid
        (C) STRANDEDNESS: unknown
        (D) TOPOLOGY: unknown (ii) MOLECULE TYPE: cDNA (iii) HYPOTHETICAL: NO (iv) ANTI-SENSE: NO (xi) SEQUENCE DESCRIPTION: SEQ ID NO: 25:

```
CC AAAACATTGA TTTCAGGGCT GCCAGGAAGG AAGAGCAGCA GCAGGGTGGG          52

AGAGAAGCTC CAGTCAGCCC ACAAGATGCC ATTGTCCCCC GGCCTCCTGC TGCTGCTGCT  112

CTCCGGGGCC ACGGCCACCG CTGCCCTGCC CCTGGAGGGT GGCCCCACCG GCCGAGACAG  172

CGAGCATATG CAGGAAGCGG CAGGAATAAG GAAAAGCAGC CTCCTGACTT TCCTCGCTTG  232

GTGGTTTGAG TGGACCTCCC AGGCCAGTGC CGGGCCCCTC ATAGGAGAGG AAGCCCGGGA  292

GGTGGCCAGG CGGCAGGAAG GCGCACCCCC CCAGCAATCC GCGCGCCGGG ACAGAATGCC  352

CTGCAGGAAC TTCTTCTGGA AGACCTTCTC CTCCTGCAAA TAAAACCTCA CCCATGAATG  412

CTCACGCAAG TGTAATGACA GACCTGAATA AAATGTATTA AGCAGCAGTG ATCTTTCCTC  472

TCCTCCTTCC CAAGTCATTG AAAAGTGTTT GTTATTTAAA TTCCAATAAT GCCCAATACT  532

GACGTGTCTT GAGTAATTTG GAACCCAAAA GTGAAGATCT TTGATAAAGA TTTTTTTTGT  592

GGTTCGACTG GACTGTGCTG AGTGCGGGCA CTGGGCTTTT CTTCTGATGT TCATTATGGT  652

GCTGGGAAGC TCTGTCTTTG ATTTAAAATA AAATAGCTAA AGGCTACAC              701
```

(2) INFORMATION FOR SEQ ID NO: 26:

(i) SEQUENCE CHARACTERISTICS:
        (A) LENGTH: 105 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 26:

```
Met Pro Leu Ser Pro Gly Leu Leu Leu Leu Leu Ser Gly Ala Thr
1               5                   10                  15

Ala Thr Ala Ala Leu Pro Leu Glu Gly Gly Pro Thr Gly Arg Asp Ser
            20                  25                  30

Glu His Met Gln Glu Ala Ala Gly Ile Arg Lys Ser Ser Leu Leu Thr
        35                  40                  45

Phe Leu Ala Trp Trp Phe Glu Trp Thr Ser Gln Ala Ser Ala Gly Pro
```

-continued

```
                50                  55                  60
Leu Ile Gly Glu Glu Ala Arg Glu Val Ala Arg Arg Gln Glu Gly Ala
65                  70                  75                  80

Pro Pro Gln Gln Ser Ala Arg Arg Asp Arg Met Pro Cys Arg Asn Phe
                85                  90                  95

Phe Trp Lys Thr Phe Ser Ser Cys Lys
            100                 105
```